(12) United States Patent
Smith et al.

(10) Patent No.: US 10,059,928 B2
(45) Date of Patent: *Aug. 28, 2018

(54) POLYMERASES

(71) Applicant: Illumina Cambridge Limited, Nr Saffron Walden (GB)

(72) Inventors: Geoffrey Paul Smith, Nr Saffron Walden (GB); Roberto Rigatti, Nr Saffron Walden (GB); Tobias William Barr Ost, Nr Saffron Walden (GB); Shankar Balasubramanian, Nr Saffron Walden (GB); Raquel Maria Sanches-Kuiper, Nr Saffron Walden (GB)

(73) Assignee: ILLUMINA CAMBRIDGE LIMITED, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,401

(22) Filed: Jun. 9, 2017

(65) Prior Publication Data

US 2017/0275602 A1    Sep. 28, 2017

Related U.S. Application Data

(63) Continuation of application No. 14/956,231, filed on Dec. 1, 2015, now abandoned, which is a continuation-in-part of application No. 14/137,434, filed on Dec. 20, 2013, now Pat. No. 9,273,352, which is a continuation of application No. 11/431,939, filed on May 10, 2006, now Pat. No. 8,623,628.

(60) Provisional application No. 60/757,997, filed on Jan. 11, 2006.

(30) Foreign Application Priority Data

May 10, 2005    (GB) .................................. 0509508.8

(51) Int. Cl.
C12N 9/12         (2006.01)
C12Q 1/686        (2018.01)

(52) U.S. Cl.
CPC ........... *C12N 9/1252* (2013.01); *C12Q 1/686* (2013.01); *C12Y 207/07007* (2013.01)

(58) Field of Classification Search
None
See application file for complete search history.

(56) References Cited

U.S. PATENT DOCUMENTS

| | | |
|---|---|---|
| 8,623,628 B2 | 1/2014 | Ost et al. |
| 9,273,352 B2 | 3/2016 | Smith et al. |
| 2016/0115461 A1 | 4/2016 | Smith et al. |

FOREIGN PATENT DOCUMENTS

| | | |
|---|---|---|
| EP | 0 701 000 B1 | 1/2001 |
| WO | WO 01/23411 A2 | 4/2001 |
| WO | WO 01/32887 A1 | 5/2001 |
| WO | WO 03/048387 A2 | 6/2003 |
| WO | WO 03/054139 A2 | 7/2003 |
| WO | WO 2004/018497 A2 | 3/2004 |
| WO | WO 2004/039947 A2 | 5/2004 |
| WO | WO 2005/024010 A1 | 3/2005 |

OTHER PUBLICATIONS

Shinkai and Loeb (Journal of Biological Chemistry, vol. 276, No. 50, pp. 46759-46764. (Year: 2001).*
Shinkai et al. (Journal of Biological Chemistry, vol. 276, No. 22, pp. 18836-18842. (Year: 2001).*
Ngo et al. In the Protein Folding Problem and Tertiary Structure Prediction, Merz et al. (ed.), Birkhauser, Boston, MA, pp. 433 and 492-495. (Year: 2004).*
Cooper et al., "Chapter 2: The Composition of Cells," in *The Cell: A Molecular Approach, Fourth Edition*. ASM Press (Ed). Sinauer Associates, Inc.: Sunderland, MA; 2007. Cover page, publisher's page, and pp. 52-53.
Dong et al., "Mutational Studies of Human DNA Polymerase Serine 867,"*Journal of Biological Chemistry*, 1993; 268:24175-182.
Dong et al., "Mutational studies of Human DNA Polymerase . . . Identification of Residues," *Journal of Biological Chemistry*, 1993; 268:24163-24174.
Doublie et al., "Crystal structure of a bacteriophage T7 DNA replication complex at 2.2 A resolution," *Nature*, 1998; 391:251-258.
Franklin et al., "Structure of the Replicating Complex of a Pol alpha Family DNA Polymerase," *Cell*, 2001; 105:657667.
Gardner et al., "Acrylic and dideoxy terminator preferences denote divergent sugar recognition by archaeon and Taq DNA polymerases," *Nucleic Acid Research*, 2002; 30(2):605-613.
Gardner et al., "Determinants of nucleotide sugar recognition in an archaeon DNA polymerase," *Nucleic Acids Research GB*, 1999; 27(12):2545-2553.
Hopfner et al., "Crystal structure of a thermostable type B DNA polymerase from Thermococcus gorgonarius," *Proc. Natl. Acad. Sci. USA*, Mar. 1999; 96:3600-3605.
Joyce et al., "Function and Structure Relationships in DNA Polymerases," Annu. Rev. Biochem., 1994; 63:777-822.
Lutz et al., "Recognition of a Non-standard Base Paid by thermostable DNA Polymerases," *Bioorganic & Medicinal Chemistry Letters*, Oxford GB, 1998; 8(10):1149-1152.
Minnick et al., "A thumb subdomain in mutant of the large fragment of *Escherichia coli* DNA polymerase I with reduced DNA binding affinity, processivity, and frameshift fidelity," *The Journal of Biological Chemistry*, 1996; 271(40):24954-24961.

(Continued)

*Primary Examiner* — Richard G Hutson
(74) *Attorney, Agent, or Firm* — Mueting, Raasch & Gebhardt, P.A.

(57) ABSTRACT

Modified DNA polymerases have an affinity for DNA such that the polymerase has an ability to incorporate one or more nucleotides into a plurality of separate DNA templates in each reaction cycle. The polymerases are capable of forming an increased number of productive polymerase-DNA complexes in each reaction cycle. The modified polymerases may be used in a number of DNA sequencing applications, especially in the context of clustered arrays.

20 Claims, 11 Drawing Sheets
Specification includes a Sequence Listing.

(56) References Cited

OTHER PUBLICATIONS

Ngo et al., "The Protein Folding Problem and Tertiary Structure Prediction," 1994, Merz et al (ed.), Birkhauser, Boston, MA, 433 and 492-495.

Polesky et al., "Identification of Residues Critical for the Polymerase Activity of the Klenow Fragment of DNA Polymerase I from *Escherichia coli*," *J. Biol. Chem.*, 1990; 265:14579-14591.

Rodriguz et al., "Crystal structure of a pol alpha family DNA polymerase from the hyperthermophilic archaeon Thermococcus . . . " *Journal of Molecular Biology GB*, 2000; 299(2):447-462.

Shinkai et al., "The Conserved Active Site Motif A of *Escherichia coli* DNA Polymerase I is Highly Mutable," *Journal of Biological Chemistry*, 2001; 276(22):18836-18842.

Shinkai and Loeb, "In Vivo Mutagenesis by *Escherichia coli* DNA Polymerase I," vol. 276, No. 50, Dec. 14, 2001, 46759-46764.

Southworth et al., "Cloning of thermostable DNA polymerases from hyperthermophilic marine archea with emphasis on *Thermococcus* sp. 9 N-7 and mutations affecting 3'-5' Exonuclease activity," *PNAS US*, 1996; 93(11):5281-5285.

Truniger et al., "Function of the C-terminus of o 29 DNA polymerase in DNA and terminal protein binding," *Nucleic Acids Research*, 2004; 32:361-370.

* cited by examiner

```
             KpnI  NdeI                                              AgeI
        GGGCGAATTGGGTACCCATATGATCTTAGATACCGACTATATCACCGAGAACGGTAAACC
  1     ---------+---------+---------+---------+---------+---------+
        CCCGCTTAACCCATGGGTATACTAGAATCTATGGCTGATATAGTGGCTCTTGCCATTTGG
                        M  I  L  D  T  D  Y  I  T  E  N  G  K  P

EcoRI                            BstBI
        GGTGATAAGGGTGTTCAAAAAGGAAAATGGCGAATTCAAGATCGAGTATGATAGAACCTT
 61     ---------+---------+---------+---------+---------+---------+
        CCACTATTCCCACAAGTTTTTCCTTTTACCGCTTAAGTTCTAGCTCATACTATCTTGGAA
        V  I  R  V  F  K  K  E  N  G  E  F  K  I  E  Y  D  R  T  F

CGAACCGTACTTCTACGCCTTGTTGAAGGACGATAGTGCCATCGAAGATGTGAAAAAAGT
121     ---------+---------+---------+---------+---------+---------+
        GCTTGGCATGAAGATGCGGAACAACTTCCTGCTATCACGGTAGCTTCTACACTTTTTTCA
        E  P  Y  F  Y  A  L  L  K  D  D  S  A  I  E  D  V  K  K  V

TACCGCCAAACGTCACGGCACCGTGGTAAAGGTTAAACGCGCCGAAAAGGTTCAGAAGAA
181     ---------+---------+---------+---------+---------+---------+
        ATGGCGGTTTGCAGTGCCGTGGCACCATTTCCAATTTGCGCGGCTTTTCCAAGTCTTCTT
        T  A  K  R  H  G  T  V  V  K  V  K  R  A  E  K  V  Q  K  K

PvuI
        GTTCCTAGGCCGTCCGATCGAGGTGTGGAAATTGTACTTTAACCATCCGCAGGATGTCCC
241     ---------+---------+---------+---------+---------+---------+
        CAAGGATCCGGCAGGCTAGCTCCACACCTTTAACATGAAATTGGTAGGCGTCCTACAGGG
        F  L  G  R  P  I  E  V  W  K  L  Y  F  N  H  P  Q  D  V  P

EcoRV            EcoRV
        GGCGATTAGAGATCGTATTCGTGCCCACCCGGCGGTAGTGGATATCTATGAGTACGATAT
301     ---------+---------+---------+---------+---------+---------+
        CCGCTAATCTCTAGCATAAGCACGGGTGGGCCGCCATCACCTATAGATACTCATGCTATA
        A  I  R  D  R  I  R  A  H  P  A  V  V  D  I  Y  E  Y  D  I

CCCGTTCGCAAAAAGATACTTGATTGATAAAGGACTAATCCCGATGGAAGGCGATGAAGA
361     ---------+---------+---------+---------+---------+---------+
        GGGCAAGCGTTTTTCTATGAACTAACTATTTCCTGATTAGGGCTACCTTCCGCTACTTCT
        P  F  A  K  R  Y  L  I  D  K  G  L  I  P  M  E  G  D  E  E

AgeI
        ATTAACCATGTTAGCGTTCTCCATCTCCACCCTGTACCACGAAGGCGAAGAGTTCGGCAC
421     ---------+---------+---------+---------+---------+---------+
        TAATTGGTACAATCGCAAGAGGTAGAGGTGGGACATGGTGCTTCCGCTTCTCAAGCCGTG
        L  T  M  L  A  F  S  I  S  T  L  Y  H  E  G  E  E  F  G  T

CGGTCCGATTCTGATGATCTCCTACGCAGACGGTAGCGAAGCACGTGTGATAACCTGGAA
481     ---------+---------+---------+---------+---------+---------+
        GCCAGGCTAAGACTACTAGAGGATGCGTCTGCCATCGCTTCGTGCACACTATTGGACCTT
        G  P  I  L  M  I  S  Y  A  D  G  S  E  A  R  V  I  T  W  K
```

FIG. 9

```
                      AatII                        BclI
     GAAAATAGACCTACCTTACGTGGACGTCGTAAGTACCGAGAAGGAGATGATCAAAAGATT
541  ------------+---------+---------+---------+---------+---------+
     CTTTTATCTGGATGGAATGCACCTGCAGCATTCATGGCTCTTCCTCTACTAGTTTTCTAA
      K  I  D  L  P  Y  V  D  V  V  S  T  E  K  E  M  I  K  R  F

BamHI
     CCTGAGGGTGGTCCGTGAGAAGGATCCGGACGTACTGATTACCTATAACGGCGATAACTT
601  ------------+---------+---------+---------+---------+---------+
     GGACTCCCACCAGGCACTCTTCCTAGGCCTGCATGACTAATGGATATTGCCGCTATTGAA
      L  R  V  V  R  E  K  D  P  D  V  L  I  T  Y  N  G  D  N  F

BglII
     CGACTTCGCCTACTTGAAAAAGAGATCTGAGGAATTAGGCATCAAATTCACCCTGGGCCG
661  ------------+---------+---------+---------+---------+---------+
     GCTGAAGCGGATGAACTTTTTCTCTAGACTCCTTAATCCGTAGTTTAAGTGGGACCCGGC
      D  F  A  Y  L  K  K  R  S  E  E  L  G  I  K  F  T  L  G  R

PflMI
     TGATGGCAGTGAGCCGAAAATCCAACGTATGGGCGACCGCTTCGCCGTCGAGGTGAAAGG
721  ------------+---------+---------+---------+---------+---------+
     ACTACCGTCACTCGGCTTTTAGGTTGCATACCCGCTGGCGAAGCGGCAGCTCCACTTTCC
      D  G  S  E  P  K  I  Q  R  M  G  D  R  F  A  V  E  V  K  G

AccI
     CCGTATACATTTCGACTTGTATCCGGTGATTAGGCGTACCATTAATTTGCCGACCTACAC
781  ------------+---------+---------+---------+---------+---------+
     GGCATATGTAAAGCTGAACATAGGCCACTAATCCGCATGGTAATTAAACGGCTGGATGTG
      R  I  H  F  D  L  Y  P  V  I  R  R  T  I  N  L  P  T  Y  T

BbsI
     CTTGGAAGCGGTGTACGAGGCGGTCTTCGGCAAGCCGAAGGAAAAGGTGTACGCCGAAGA
841  ------------+---------+---------+---------+---------+---------+
     GAACCTTCGCCACATGCTCCGCCAGAAGCCGTTCGGCTTCCTTTTCCACATGCGGCTTCT
      L  E  A  V  Y  E  A  V  F  G  K  P  K  E  K  V  Y  A  E  E

XbaI
     GATCGCGCAGGCGTGGGAGAGCGGTGAGGGTCTAGAACGTGTTGCAAGATATAGCATGGA
901  ------------+---------+---------+---------+---------+---------+
     CTAGCGCGTCCGCACCCTCTCGCCACTCCCAGATCTTGCACAACGTTCTATATCGTACCT
      I  A  Q  A  W  E  S  G  E  G  L  E  R  V  A  R  Y  S  M  E

GGACGCCAAAGTTACCTACGAATTGGGCCGCGAGTTTTTTCCGATGGAGGCCCAGTTATC
961  ------------+---------+---------+---------+---------+---------+
     CCTGCGGTTTCAATGGATGCTTAACCCGGCGCTCAAAAAAGGCTACCTCCGGGTCAATAG
      D  A  K  V  T  Y  E  L  G  R  E  F  F  P  M  E  A  Q  L  S

TCGTTTAATTGGCCAGTCCCTGTGGGATGTTAGCCGCAGTTCTACTGGTAATTTGGTAGA
1021 ------------+---------+---------+---------+---------+---------+
     AGCAAATTAACCGGTCAGGGACACCCTACAATCGGCGTCAAGATGACCATTAAACCATCT
      R  L  I  G  Q  S  L  W  D  V  S  R  S  S  T  G  N  L  V  E

ATGGTTCTTACTGCGCAAAGCGTATAAACGTAACGAGTTAGCGCCAAATAAGCCGGACGA
1081 ------------+---------+---------+---------+---------+---------+
     TACCAAGAATGACGCGTTTCGCATATTTGCATTGCTCAATCGCGGTTTATTCGGCCTGCT
      W  F  L  L  R  K  A  Y  K  R  N  E  L  A  P  N  K  P  D  E

ACGTGAACTGGCCCGTCGTCGTGGTGGCTATGCCGGCGGTTACGTGAAGGAACCGGAGCG
1141 ------------+---------+---------+---------+---------+---------+
     TGCACTTGACCGGGCAGCAGCACCACCGATACGGCCGCCAATGCACTTCCTTGGCCTCGC
      R  E  L  A  R  R  R  G  G  Y  A  G  G  Y  V  K  E  P  E  R
```

FIG. 9 CONT'D

```
      TGGCCTATGGGATAACATTGTGTACCTTGACTTTAGAAGCTATGCGGTTAGCATCATCAT
1201  ----------+---------+---------+---------+---------+---------+
      ACCGGATACCCTATTGTAACACATGGAACTGAAATCTTCGATACGCCAATCGTAGTAGTA
       G  L  W  D  N  I  V  Y  L  D  F  R  S  Y  A  V  S  I  I  I

AatII
      CACCCATAATGTTAGTCCGGACACATTGAATCGTGAAGGATGCAAAGAATATGACGTCGC
1261  ----------+---------+---------+---------+---------+---------+
      GTGGGTATTACAATCAGGCCTGTGTAACTTAGCACTTCCTACGTTTCTTATACTGCAGCG
       T  H  N  V  S  P  D  T  L  N  R  E  G  C  K  E  Y  D  V  A

CCCAGAGGTGGGCCACAAATTTTGTAAAGATTTCCCAGGATTCATCCCAAGTTTGTTGGG
1321  ----------+---------+---------+---------+---------+---------+
      GGGTCTCCACCCGGTGTTTAAAACATTTCTAAAGGGTCCTAAGTAGGGTTCAAACAACCC
       P  E  V  G  H  K  F  C  K  D  F  P  G  F  I  P  S  L  L  G

TGATCTGCTGGAAGAACGCCAGAAAATCAAACGTAAGATGAAGGCGACCGTCGATCCACT
1381  ----------+---------+---------+---------+---------+---------+
      ACTAGACGACCTTCTTGCGGTCTTTTAGTTTGCATTCTACTTCCGCTGGCAGCTAGGTGA
       D  L  L  E  E  R  Q  K  I  K  R  K  M  K  A  T  V  D  P  L

BclI            EcoRI
      GGAGAAAAAGCTATTGGACTACCGTCAGCGCCTGATCAAGATTTTGGCGAATTCTTTCTA
1441  ----------+---------+---------+---------+---------+---------+
      CCTCTTTTTCGATAACCTGATGGCAGTCGCGGACTAGTTCTAAAACCGCTTAAGAAAGAT
       E  K  K  L  L  D  Y  R  Q  R  L  I  K  I  L  A  N  S  F  Y

TGGATACTACGGCTACGCCAAAGCCCGTTGGTATTGTAAAGAGTGCGCCGAGTCTGTCAC
1501  ----------+---------+---------+---------+---------+---------+
      ACCTATGATGCCGATGCGGTTTCGGGCAACCATAACATTTCTCACGCGGCTCAGACAGTG
       G  Y  Y  G  Y  A  K  A  R  W  Y  C  K  E  C  A  E  S  V  T

TGCCTGGGGTCGTGAATATATCGAAATGGTGATCCGCGAGCTGGAAGAGAAATTTGGATT
1561  ----------+---------+---------+---------+---------+---------+
      ACGGACCCCAGCACTTATATAGCTTTACCACTAGGCGCTCGACCTTCTCTTTAAACCTAA
       A  W  G  R  E  Y  I  E  M  V  I  R  E  L  E  E  K  F  G  F

BsaI
      CAAAGTCTTGTACGCCGATACCGATGGTCTGCACGCGACCATTCCGGGTGCCGATGCCGA
1621  ----------+---------+---------+---------+---------+---------+
      GTTTCAGAACATGCGGCTATGGCTACCAGACGTGCGCTGGTAAGGCCCACGGCTACGGCT
       K  V  L  Y  A  D  T  D  G  L  H  A  T  I  P  G  A  D  A  E

GACCGTGAAGAAAAAGGCGAAAGAGTTTTTGAAATATATCAATCCGAAGTTGCCGGGATT
1681  ----------+---------+---------+---------+---------+---------+
      CTGGCACTTCTTTTTCCGCTTTCTCAAAAACTTTATATAGTTAGGCTTCAACGGCCCTAA
       T  V  K  K  K  A  K  E  F  L  K  Y  I  N  P  K  L  P  G  L

ATTAGAATTGGAATACGAAGGTTTCTATGTTCGCGGCTTTTTCGTGACCAAGAAAAAATA
1741  ----------+---------+---------+---------+---------+---------+
      TAATCTTAACCTTATGCTTCCAAAGATACAAGCGCCGAAAAAGCACTGGTTCTTTTTTAT
       L  E  L  E  Y  E  G  F  Y  V  R  G  F  F  V  T  K  K  K  Y

XbaI
      CGCCGTGATCGACGAGGAAGGAAAAATTACCACCCGTGGTCTAGAGATTGTTCGTCGTGA
1801  ----------+---------+---------+---------+---------+---------+
      GCGGCACTAGCTGCTCCTTCCTTTTTAATGGTGGGCACCAGATCTCTAACAAGCAGCACT
       A  V  I  D  E  E  G  K  I  T  T  R  G  L  E  I  V  R  R  D
```

FIG. 9 CONT'D

```
              CTGGTCCGAAATCGCCAAAGAAACCCAGGCCCGTGTACTGGAAGCGATTTTGAAGCATGG
       1861   ------------+----------+----------+----------+----------+----------+
              GACCAGGCTTTAGCGGTTTCTTTGGGTCCGGGCACATGACCTTCGCTAAAACTTCGTACC
               W  S  E  I  A  K  E  T  Q  A  R  V  L  E  A  I  L  K  H  G

CGATGTGGAGGAGGCGGTTCGTATCGTCAAAGAAGTGACCGAAAAGCTGAGCAAGTATGA
       1921   ------------+----------+----------+----------+----------+----------+
              GCTACACCTCCTCCGCCAAGCATAGCAGTTTCTTCACTGGCTTTTCGACTCGTTCATACT
               D  V  E  E  A  V  R  I  V  K  E  V  T  E  K  L  S  K  Y  E

BspMI
              AGTGCCGCCGGAGAAATTGGTCATACACGAACAAATCACACGTGACCTGCGCGATTATAA
       1981   ------------+----------+----------+----------+----------+----------+
              TCACGGCGGCCTCTTTAACCAGTATGTGCTTGTTTAGTGTGCACTGGACGCGCTAATATT
               V  P  P  E  K  L  V  I  H  E  Q  I  T  R  D  L  R  D  Y  K

AgeI
              GGCGACCGGTCCGCACGTTGCCGTGGCGAAGCGTTTGGCGGCCCGTGGTGTTAAGATTCG
       2041   ------------+----------+----------+----------+----------+----------+
              CCGCTGGCCAGGCGTGCAACGGCACCGCTTCGCAAACCGCCGGGCACCACAATTCTAAGC
               A  T  G  P  H  V  A  V  A  K  R  L  A  A  R  G  V  K  I  R

BstEII
              TCCAGGAACCGTGATTAGTTACATAGTGTTGAAGGGCAGTGGTCGTATTGGTGACCGTGC
       2101   ------------+----------+----------+----------+----------+----------+
              AGGTCCTTGGCACTAATCAATGTATCACAACTTCCCGTCACCAGCATAACCACTGGCACG
               P  G  T  V  I  S  Y  I  V  L  K  G  S  G  R  I  G  D  R  A

CATCCCGGCGGATGAGTTTGACCCGACCAAGCATCGTTATGACGCCGAATATTATATCGA
       2161   ------------+----------+----------+----------+----------+----------+
              GTAGGGCCGCCTACTCAAACTGGGCTGGTTCGTAGCAATACTGCGGCTTATAATATAGCT
               I  P  A  D  E  F  D  P  T  K  H  R  Y  D  A  E  Y  Y  I  E

BspMI
                                                                       BbsI
              GAATCAGGTGCTACCAGCGGTTGAACGTATTTTGAAGGCATTCGGCTATCGTAAAGAAGA
       2221   ------------+----------+----------+----------+----------+----------+
              CTTAGTCCACGATGGTCGCCAACTTGCATAAAACTTCCGTAAGCCGATAGCATTTCTTCT
               N  Q  V  L  P  A  V  E  R  I  L  K  A  F  G  Y  R  K  E  D

BspMI
              CCTGCGCTACCAGAAAACCAAGCAGGTTGGTCTGGGTGCCTGGTTGAAAGTGAAAGGCAA
       2281   ------------+----------+----------+----------+----------+----------+
              GGACGCGATGGTCTTTTGGTTCGTCCAACCAGACCCACGGACCAACTTTCACTTTCCGTT
               L  R  Y  Q  K  T  K  Q  V  G  L  G  A  W  L  K  V  K  G  K

NheI    SacI
              AAAATAAGCTAGCGGAGCTCCAGCTTTTGTTCCC
       2341   ------------+----------+----------+-----
              TTTTATTCGATCGCCTCGAGGTCGAAAACAAGGG
               K  *
```

FIG. 9 CONT'D

POLYMERASES

RELATED APPLICATIONS

The present application is a continuation application of U.S. patent application Ser. No. 14/956,231, filed Dec. 1, 2015, which is a continuation-in-part application of U.S. patent application Ser. No. 14/137,434, filed Dec. 20, 2013, now issued as U.S. Pat. No. 9,273,352 on Mar. 1, 2016, which is a continuation application of U.S. patent application Ser. No. 11/431,939, filed May 10, 2006, now issued as U.S. Pat. No. 8,623,628 on Jan. 7, 2014, which claims priority from U.S. Provisional Application 60/757,997, filed Jan. 11, 2006, and Great Britain Provisional Application No. 0509508.8, filed May 10, 2005. Applicants claim the benefits of priority under 35 U.S.C. § 119 as to the United States and Great Britain applications, and the entire disclosures of each of these applications are incorporated herein by reference in their entireties.

FIELD OF THE INVENTION

The present invention relates to polymerase enzymes and more particularly to modified DNA polymerases having an affinity for DNA such that the polymerase has an ability to incorporate a nucleotide or nucleotides into a plurality of separate DNA templates in each reaction cycle and is capable of forming an increased number of productive polymerase-DNA complexes in each reaction cycle. Also included in the scope of the present invention are methods of using the modified polymerases for DNA sequencing, especially in the context of clustered arrays.

BACKGROUND

Several publications and patent documents are referenced in this application in order to more fully describe the state of the art to which this invention pertains. The disclosure of each of these publications and documents is incorporated by reference herein.

The three-dimensional crystal structure of certain DNA polymerases has revealed three separate subdomains, named palm, fingers and thumb (Joyce, C. M. and Steiz, T. A. (1994) Function and structure relationships in DNA polymerases, Annu. Rev. Biochem., 63, 777-822), each having key roles during DNA polymerisation.

The C terminal thumb subdomain of DNA polymerases has been implicated in DNA binding and processivity (Doublie et al. 1998. Nature 391, 251; Truniger et al. 2004. Nucleic Acids Research 32, 371). Residues in this region of DNA polymerases interact with the primer:template duplex.

Disruption of the structure of this region either by the introduction of site-directed mutations or truncation by the deletion of a small number of amino acids, has provided evidence for variants with reduced DNA affinity and processivity without gross changes in other physical properties such as dNTP affinity and nucleotide insertion fidelity (Truniger et al. 2004. Nucleic Acids Research 32, 371; Minnick et al. 1996. J. Biol. Chem., 271, 24954; Polesky et al. 1990. J. Biol. Chem., 265, 14579).

Polymerases may be separated into two structurally distinct families called family A and family B.

The C-terminal subdomain of family B polymerases has been poorly studied, but is believed to be involved in DNA binding based primarily on the inspection of the x-ray crystal structure of the closed form (DNA-bound) of polymerase RB69. Mutagenesis studies have been conducted within this thumb domain for two examples of the family B class, namely Phi29 and T4. However, these studies were limited to amino acid deletions of large portions of the domain. The same type of deletion has been carried out for Klenow (a family A polymerase). The performance of the variants in these studies was evaluated in terms of their ability to bind and incorporate dNTPs, the effect the deletion had on fidelity, their affinity for DNA and also their interaction with accessory proteins.

No studies of the thumb domain of the polymerase from a thermophilic archaeon have previously been carried out.

The subject matter of the present invention was presented in prior filed U.K. Provisional Application No. 0509508.8 filed May 10, 2005, priority of which is believed to be available under 35 U.S.C. § 119, and the disclosure of which is incorporated herein in its entirety. In said application, the structural aspects of the polymerases and the related materials of the present invention were disclosed as they are herein, and were accompanied by information providing further background and characterization of function, which was also in accordance with the understanding of the inventors at the time. Since filing said application, further study of the enzymes in question has taken place and additional data illustrating and advancing the understanding of their function and application, has resulted, which is now felt to be desirably presented herein.

Accordingly, it is toward the advancement of the understanding and application of the present invention that the present application is directed.

SUMMARY OF THE INVENTION

The present invention is based upon the realisation that the tight binding of a polymerase to the DNA template is not always an advantageous property. This is particularly the case in the context of sequencing reactions in which only a single nucleotide incorporation event is required in each reaction cycle. Thus, for a polymerase that binds tightly to DNA, the ability of the polymerase to take part in incorporation of nucleotides on multiple DNA strands is restricted compared to a variant polymerase that has a lower affinity for DNA.

The present inventors have devised a method for sequencing DNA that uses nucleotide analogues bearing modifications at the 3' sugar hydroxyl group which block incorporation of further nucleotides (see WO03/048387, for example, and the citations described therein). The use of nucleotides bearing a 3' block allows successive nucleotides to be incorporated into a polynucleotide chain in a controlled manner. After each nucleotide addition the presence of the 3' block prevents incorporation of a further nucleotide into the chain. Once the nature of the incorporated nucleotide has been determined, the block may be removed, leaving a free 3' hydroxyl group for addition of the next nucleotide.

In addition, in the context of reactions such as sequencing reactions involving modified nucleotides (as discussed above and in more detail herein below), tight binding of a polymerase may in fact present certain disadvantages in terms of reaction completion. For example, if an inactive polymerase molecule having a tight DNA binding affinity forms a stable complex with a template DNA molecule, no extension is possible from that particular template DNA molecule.

With this realisation, the present invention provides altered polymerases which have a weaker interaction with template DNA. Thus, the polymerase of the invention has an improved ability to move from one template DNA molecule to another during a reaction cycle. This ability to form an increased number of productive polymerase-DNA complexes has the benefit that levels or reaction completion in reactions involving addition of a single nucleotide in each reaction cycle are much improved.

Unmodified polymerases tend to bind DNA with high affinity such that the equation:

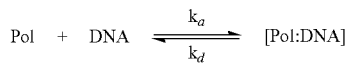

is heavily shifted to favour the [Pol:DNA] complex.

In contrast, in the present invention, the altered polymerases bind to DNA less well, meaning that the equilibrium position is shifted towards the left hand side.

Therefore, the invention provides an altered polymerase having reduced affinity for DNA such that the polymerase has an ability to incorporate a nucleotide or nucleotides into a plurality of separate DNA templates in each reaction cycle.

By "DNA template" is meant any DNA molecule which may be bound by the polymerase and utilised as a template for nucleic acid synthesis.

"Nucleotide" is defined herein to include both nucleotides and nucleosides. Nucleosides, as for nucleotides, comprise a purine or pyrimidine base linked glycosidically to ribose or deoxyribose, but they lack the phosphate residues which would make them a nucleotide. Synthetic and naturally occurring nucleotides are included within the definition. Labelled nucleotides are included within the definition. The advantageous properties of the polymerases are due to their reduced affinity for the DNA template in combination with a retained affinity and fidelity for the nucleotides which they incorporate.

In one preferred aspect, an altered polymerase is provided having a reduced affinity for DNA such that the polymerase has an ability to incorporate at least one synthetic nucleotide into a plurality of DNA templates in each reaction cycle. Prior to the present invention, the problem of modifying a polymerase adapted to incorporate non-natural nucleotides, to reduce its DNA affinity whilst retaining its advantageous properties has neither been realised nor addressed.

In one embodiment, nucleotides comprise dideoxy nucleotide triphosphates (ddNTPs) such as those used in Sanger sequencing reactions. These nucleotides may be labelled, e.g., with any of a mass label, radiolabel or a fluorescent label.

In a further embodiment, the nucleotides comprise nucleotides which have been modified at the 3' sugar hydroxyl such that the substituent is larger in size than the naturally occurring 3' hydroxyl group, compared to a control polymerase.

In a preferred embodiment, the nucleotides comprise those having a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

The nucleosides or nucleotides which are incorporated by the polymerases of the present invention according to one embodiment, comprise a purine or pyrimidine base and a ribose or deoxyribose sugar moiety which has a blocking group covalently attached thereto, preferably at the 3'O position, which renders the molecules useful in techniques requiring blocking of the 3'-OH group to prevent incorporation of additional nucleotides, such as for example in sequencing reactions, polynucleotide synthesis, nucleic acid amplification, nucleic acid hybridisation assays, single nucleotide polymorphism studies, and other such techniques.

Once the blocking group has been removed, it is possible to incorporate another nucleotide to the free 3'-OH group.

Preferred modified nucleotides are exemplified in International Patent Application publication number WO 2004/018497 in the name of Solexa Limited, which reference is incorporated herein in its entirety.

In a preferred embodiment the R' group of the modified nucleotide or nucleoside is an alkyl or substituted alkyl. In a further embodiment the —Z group of the modified nucleotide or nucleoside is of formula —C(R')$_2$—N$_3$. In a most preferred embodiment the modified nucleotide or nucleoside includes a Z group which is an azido methyl group.

The preferred polymerases of the invention, as discussed in detail below, are particularly preferred for incorporation of nucleotide analogues wherein Z is an azido methyl group.

The modified nucleotide can be linked via the base to a detectable label by a desirable linker, which label may be a fluorophore, for example. The detectable label may instead, if desirable, be incorporated into the blocking groups of formula "Z". The linker can be acid labile, photolabile or contain a disulfide linkage. Other linkages, in particular phosphine-cleavable azide-containing linkers, may be employed in the invention as described in greater detail in WO 2004/018497, the contents of which are incorporated herein in their entirety.

Preferred labels and linkages include those disclosed in WO 03/048387, which is incorporated herein in its entirety.

In one embodiment the modified nucleotide or nucleoside has a base attached to a detectable label via a cleavable linker, characterised in that the cleavable linker contains a moiety selected from the group consisting of:

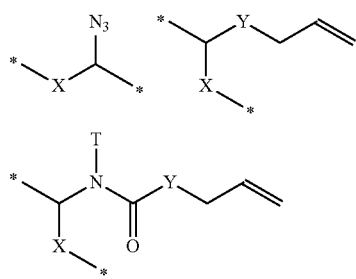

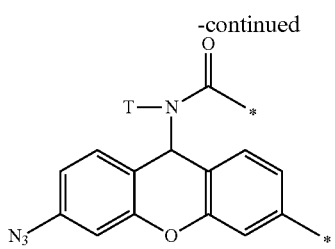

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of the nucleotide or nucleoside).

In one embodiment the detectable label comprises a fluorescent label. Suitable fluorophores are well known in the art. In a preferred embodiment each different nucleotide type will carry a different fluorescent label. This facilitates the identification and incorporation of a particular nucleotide. Thus, for example modified Adenine, Guanine, Cytosine and Thymine would all have attached a separate fluorophore to allow them to be discriminated from one another readily. Surprisingly, it has been found that the altered polymerases are capable of incorporating modified nucleotide analogues carrying a number of different fluorescent labels. Moreover, the polymerases are capable of incorporating all four bases. These properties provide substantial advantages with regard to the use of the polymerases of the present invention in nucleic acid sequencing protocols.

As aforesaid, preferred nucleotide analogues include those containing O-azido methyl functionality at the 3' position. It will be appreciated that for other nucleotide analogues the preferred amino acid sequence of the polymerase in the C terminal thumb sub-domain region, which contributes significantly to DNA binding, for optimum incorporation may vary. For any given nucleotide analogue, optimum sequence preferences in the C terminal thumb sub domain region (such as at residues Lys 790, 800, 844, 874, 878 and Arg 806 in RB69 and at residues Arg 743, Arg 713 and Lys 705 in 9°N polymerase, as discussed in greater detail below) may be determined by experiment, for example by construction of a library or discrete number of mutants followed by testing of individual variants in an incorporation assay system.

As aforementioned, the altered polymerases of the invention are capable of improved incorporation of all nucleotides, including a wide range of modified nucleotides having large 3' substituent groups of differing sizes and of varied chemical nature. The advantageous properties of the polymerases are due to their reduced affinity for the DNA template leading to increased dissociation of the polymerase from the DNA without adverse effects on affinity and fidelity for the nucleotides which they incorporate.

By virtue of the decreased DNA binding affinity of the polymerase of the invention, it is able to incorporate one or more nucleotides into several different DNA molecules in a single reaction cycle. Thus, the overall efficiency of reaction is improved, leading to greater levels of completion.

By "a reaction cycle" is meant a suitable reaction period to allow the incorporation of nucleotides into the template. Exemplary conditions for a single reaction cycle are one 30 minute, 45° C. incubation period.

Many polymerisation reactions occur in the presence of an excess of DNA compared to polymerase. The polymerase of the present invention allows such a polymerisation reaction to proceed more effectively since the polymerase can catalyse numerous rounds of incorporation of a nucleotide or nucleotides on separate template DNA molecules. An unaltered polymerase on the other hand, particularly one which binds DNA much more tightly, will not have this ability since it is more likely to only participate in nucleotide incorporation on a single template in each reaction cycle. The polymerase according to the present invention allows high levels of reaction completion under conditions where the concentration of polymerase is limiting with respect to the concentration of DNA. In particular, the polymerase presents improved ability to incorporate one or more nucleotides into separate DNA molecules under conditions wherein the DNA:polymerase ratio is at least about 2:1, 3:1 or 5:1. However, at high concentrations of polymerase, the improvement may be masked.

Thus, an altered polymerase is provided having an affinity for DNA such that the polymerase is capable of forming an increased number of productive polymerase-DNA complexes in each reaction cycle.

The improved properties of the polymerases of the invention may be compared to a suitable control. "Control polymerase" is defined herein as the polymerase against which the activity of the altered polymerase is compared. The control polymerase is of the same type as the altered polymerase but does not carry the alteration(s) which reduce affinity of the polymerase for DNA. Thus, in a particular embodiment, the control polymerase is a 9°N polymerase and the modified polymerase is the same 9°N polymerase except for the presence of one or more modifications which reduce the affinity of the 9°N polymerase for DNA.

In one embodiment, the control polymerase is a wild type polymerase which is altered to provide an altered polymerase which can be directly compared with the unaltered polymerase.

In one embodiment, the control polymerase comprises substitution mutations at positions which are functionally equivalent to Leu408 and Tyr409 and Pro410 in the 9°N DNA polymerase amino acid sequence. Thus, in this embodiment the control polymerase has a substitution mutation at position 408 from leucine to a different amino acid, at position 409 from tyrosine to a different amino acid and at position 410 from proline to a different amino acid or at positions which are functionally equivalent if the polymerase is not a 9°N DNA polymerase. In a preferred embodiment, the control polymerase is a 9°N DNA polymerase comprising the said substitution mutations.

In another embodiment, the control polymerase comprises substitution mutations which are functionally equivalent to Leu408Tyr and Tyr409Ala and Pro410Val in the 9°N DNA polymerase amino acid sequence. Thus, in this embodiment the control polymerase has a substitution mutation at position 408 from leucine to tyrosine, at position 409 from tyrosine to alanine and at position 410 from proline to valine or at positions which are functionally equivalent if the polymerase is not a 9°N DNA polymerase. In a preferred embodiment, the control polymerase is a 9°N DNA polymerase comprising the above substitution mutations.

The control polymerase may further comprise a substitution mutation at the position functionally equivalent to Cys223 in the 9°N DNA polymerase amino acid sequence. Thus, in this embodiment the control polymerase has a substitution mutation at position 223 from cysteine to a different amino acid, or at a position which is functionally equivalent if the polymerase is not a 9°N DNA polymerase. In a preferred embodiment, the control polymerase is a 9°N DNA polymerase comprising the said substitution mutation. In another embodiment, the control polymerase comprises the substitution mutation functionally equivalent to Cys223Ser in the 9°N DNA polymerase amino acid sequence. Thus, in this embodiment the control polymerase has a substitution mutation at position 223 from cysteine to serine, or at a position which is functionally equivalent if the polymerase is not a 9°N DNA polymerase. In a preferred embodiment, the control polymerase is a 9°N DNA polymerase comprising the said substitution mutation.

Preferably, the control polymerase is a 9°N DNA polymerase comprising a combination of the above mentioned mutations.

The altered polymerase will generally have a reduced affinity for DNA. This may be defined in terms of dissociation constant. Thus, wild type polymerases tend to have dissociation constants in the nano-picomolar range. For the purposes of the present invention, an altered polymerase having an affinity for DNA which is reduced compared to the control unaltered polymerase is suitable. Preferably, due to the alteration(s), the polymerase has at least a, or approximately a 2-fold, 3-fold, 4-fold or 5-fold etc., increase in its dissociation constant when compared to the control unaltered polymerase.

By "functionally equivalent" is meant the amino acid substitution that is considered to occur at the amino acid position in another polymerase that has the same functional role in the enzyme. As an example, the mutation at position 412 from Tyrosine to Valine (Y412V) in the Vent DNA polymerase would be functionally equivalent to a substitution at position 409 from Tyrosine to Valine (Y409V) in the 9°N polymerase. The bulk of this amino acid residue is thought to act as a "steric gate" to block access of the 2'-hydroxyl of the nucleotide sugar to the binding site. Also, residue 488 in Vent polymerase is deemed equivalent to amino acid 485 in 9°N polymerase, such that the Alanine to Leucine mutation at 488 in Vent (A488L) is deemed equivalent to the A485L mutation in 9°N polymerase.

Generally, functionally equivalent substitution mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different polymerases on the basis of sequence alignment and/or molecular modelling.

The altered polymerase will generally be an "isolated" or "purified" polypeptide. By "isolated polypeptide" is meant a polypeptide that is essentially free from contaminating cellular components, such as carbohydrates, lipids, nucleic acids or other proteinaceous impurities which may be associated with the polypeptide in nature. Typically, a preparation of the isolated polymerase contains the polymerase in a highly purified form, i.e. at least about 80% pure, preferably at least about 90% pure, more preferably at least about 95% pure, more preferably at least about 98% pure and most preferably at least about 99% pure. Purity of a preparation of the enzyme may be assessed, for example, by appearance of a single band on a standard SDS-polyacrylamide electrophoresis gel.

The altered polymerase may be a "recombinant" polypeptide.

The altered polymerase according to the invention may be any DNA polymerase. More particularly, the altered polymerase may be a family B type DNA polymerase, or a mutant or variant thereof. Family B DNA polymerases include numerous archael DNA polymerase, human DNA polymerase α and T4, RB69 and #29 phage DNA polymerases. These polymerases are less well studied than the family A polymerases, which include polymerases such as Taq, and T7 DNA polymerase. In one embodiment the polymerase is selected from any family B archael DNA polymerase, human DNA polymerase α or T4, RB69 and φ29 phage DNA polymerases.

The archael DNA polymerases are in many cases from hyperthermophilic archea, which means that the polymerases are often thermostable. Accordingly, in a further preferred embodiment the polymerase is a thermophilic archaeon polymerase, including, e.g., Vent, Deep Vent, 9°N and Pfu polymerase. Vent and Deep Vent are commercial names used for family B DNA polymerases isolated from the hyperthermophilic archaeon *Thermococcus litoralis* and *Pyrococcus furiosus* respectively. 9°N polymerase was also identified from *Thermococcus* sp. Pfu polymerase was isolated from *Pyrococcus furiosus*. As mentioned above, prior to the present invention the thumb domain from a thermophilic polymerase had not been studied. A preferred polymerase of the present invention is 9°N polymerase, including mutants and variants thereof. 9°N polymerase has no requirement for accessory proteins. This can be contrasted with previously studied polymerases in which deletions in the thumb domain were shown to adversely affect the interaction with accessory proteins whilst not altering other properties of the polymerase. In contrast, as is shown in the Experimental Section below, a deletion of a large number of residues of 9°N has a significant adverse effect on the important properties of 9°N such that catalytic activity is severely compromised.

It is to be understood that the invention is not intended to be limited to mutants or variants of the family B polymerases. The altered polymerase may also be a family A polymerase, or a mutant or variant thereof, for example a mutant or variant Taq or T7 DNA polymerase enzyme, or a polymerase not belonging to either family A or family 8, such as for example reverse transcriptases.

A number of different types of alterations are contemplated by the invention, wherein such alterations produce a polymerase displaying the desired properties as a result of reduced affinity for DNA. Particularly preferred are substitution mutations in the primary amino acid sequence of the polymerase, although addition and deletion mutations may also produce useful polymerases. Suitable alteration techniques, such as site directed mutagenesis, e.g., are well known in the art.

Thus, by "altered polymerase" it is meant that the polymerase has at least one amino acid change compared to the control polymerase enzyme. In general this change will comprise the substitution of at least one amino acid for another. In preferred embodiments, these changes are non-conservative changes, although conservative changes to maintain the overall charge distribution of the protein are also envisaged in the present invention. Moreover, it is within the contemplation of the present invention that the modification in the polymerase sequence may be a deletion or addition of one or more amino acids from or to the protein, provided that the resultant polymerase has reduced DNA affinity and an ability to incorporate a nucleotide or nucleotides into a plurality of separate DNA templates in each reaction cycle compared to a control polymerase.

In one embodiment, the alteration to form the polymerase of the invention comprises at least one mutation, and preferably at least one substitution mutation, at a residue in the polymerase which destabilises the interaction of the polymerase with DNA. Thus, the resultant polymerase interacts in a less stable manner with DNA. As aforementioned, a decrease in affinity of the polymerase for DNA allows it to incorporate one or more nucleotides into several different DNA molecules in a single reaction cycle. Thus, the overall efficiency of a reaction is improved, leading to greater levels of reaction completion.

In a further embodiment, the alteration comprises at least one mutation, and preferably at least one substitution mutation, at a residue in the polymerase which binds to DNA. Suitable target residues for mutation can be selected according to available crystal structures for suitable polymerases, particularly when crystallised in the closed state (bound to DNA). By reducing the number of binding contacts with the DNA, an overall reduction in DNA binding affinity may be achieved. Thus, the resultant polymerase displays improved characteristics in the context of nucleotide incorporation reactions in which tight binding to DNA is disadvantageous.

In similar fashion, the polymerase may also carry an alteration which comprises at least one mutation, and preferably at least one substitution mutation, at a residue in the DNA binding domain of the polymerase. Such a mutation is predicted to decrease the DNA binding affinity of the altered polymerase such that it is able to more readily bind to and dissociate from separate template DNA molecules during a reaction.

In one embodiment, the polymerase includes an alteration which comprises at least one mutation, and preferably at least one substitution mutation, at a basic amino acid residue in the polymerase. Indeed, many positively charged amino acid residues in polymerases are known to interact with the overall negatively charged DNA double helix, in particular with specific phosphate groups of nucleotides in the DNA.

As aforementioned, a particular type of alteration resulting in a polymerase according to the invention comprises at least one substitution mutation. As is shown in the experimental section below, deletion of residues from the polymerase amino acid sequence generate a polymerase which, whilst having a reduced affinity for DNA, does not have overall advantageous properties since catalytic ability is impaired. In one particularly preferred embodiment, the polymerase comprises two substitution mutations, but may contain four, five, six or seven, etc. mutations provided that the resultant polymerase has the desired properties.

Preferably, the affinity of the polymerase for nucleotides is substantially unaffected by the alteration. As is shown in the experimental section (in particular example 6), it is possible to mutate a polymerase such that its affinity for DNA is reduced, whilst the affinity of the polymerase for a nucleotide, which may be a dNTP or ddNTP or a modified version thereof for example (see the definition of nucleotide supra) is not adversely affected. By "substantially unaffected" in this context is meant that the affinity for the nucleotide remains of the same order as for the unaltered polymerase. Preferably, the affinity for nucleotides is unaffected by the alteration.

Preferably, the fidelity of the polymerase is substantially unaffected by the alteration. As is shown in the experimental section (in particular example 6), it is possible to mutate a polymerase such that its affinity for DNA is reduced, whilst the fidelity of the polymerase is substantially unaffected by the alteration. By "substantially unaffected" in this context is meant that the misincorporation frequency for each nucleotide remains of the same order as for the unaltered polymerase. Preferably, the fidelity of the polymerase is unaffected by the alteration.

In terms of specific and preferred structural mutants, these may be based upon the most preferred polymerase, namely 91 DNA polymerase. As discussed in example 1 below, an energy minimised overlaid alignment (contracted by Cresset) of the crystal structures of the open form of 9°N-7 DNA polymerase (PDB=1qht), the open structure of a closely related DNA polymerase RB69 (PDB=1ih7) and the closed form of RB69 (PDB=1ig9) was used as a structural model for the identification of key residues involved in DNA binding. Accordingly, an altered polymerase is provided which comprises or incorporates one, two or three amino acid substitution mutations to a different amino acid at the position or positions functionally equivalent to Lys705, Arg713 and/or Arg743 in the 9°N DNA polymerase amino acid sequence. Preferably, the polymerase is a 9°N DNA polymerase comprising these mutations. All combinations and permutations of one, two or three mutations are contemplated within the scope of the invention.

Mutations may also be made at other specific residues based upon alignment of the "open" 9°N DNA polymerase structure (i.e. not bound to DNA) with the known crystal structure of the RB69 polymerase complexed with DNA. Thus, an altered polymerase is provided which comprises or incorporates one or two amino acid substitution mutations to a different amino acid at the position or positions functionally equivalent to Arg606 and/or His679 in the 9°N DNA polymerase amino acid sequence. Preferably, the polymerase is a 9°N DNA polymerase comprising these mutations. All combinations and permutations of different mutations are contemplated within the scope of the invention. Thus, these mutations may be made in combination with the other mutations discussed supra.

In one preferred embodiment, the polymerase comprises at least a substitution mutation to a different amino acid at the position functionally equivalent to either Arg713 or Arg743 in the 9°N DNA polymerase amino acid sequence. These two positions represent particularly preferred sites for mutation, as discussed in more detail in the experimental section below. Both residues may be mutated in the same polymerase to a different amino acid.

In terms of the nature of the different amino acid, the substitution mutation or mutations preferably convert the substituted amino acid to a non-basic amino acid (i.e. not lysine or arginine). Any non-basic amino acid may be chosen. Preferred substitution mutation or mutations convert the substituted amino acid to an amino acid selected from:
(i) acidic amino acids,
(ii) aromatic amino acids, particularly tyrosine (Y) or phenylalanine (F); and
(iii) non-polar amino acids, particularly, alanine (A), glycine (G) or methionine (M).

In one embodiment, the substitution mutation or mutations convert the substituted amino acid to alanine. In a more specific embodiment, an altered polymerase is provided comprising the substitution mutation or mutations which are functionally equivalent to Lys705Ala and/or Arg713Ala and/or Arg743Ala in the 9°N DNA polymerase amino acid sequence. Thus, in this embodiment the polymerase has a substitution mutation at position 705 from lysine to alanine and/or at position 713 from arginine to alanine and/or at position 743 from arginine to alanine or at positions which are functionally equivalent if the polymerase is not a 9°N DNA polymerase. In a preferred embodiment, the polymerase is a 9°N DNA polymerase comprising the said substitution mutations.

In one embodiment, the altered polymerase comprises the amino acid substitution functionally equivalent to Arg713Ala; in a further embodiment, the altered polymerase comprises the amino acid substitution functionally equivalent to Arg743Ala. Preferably, the altered polymerase is a 9°N DNA polymerase.

Specific structural mutants may also be based upon other types of polymerase, such as the RB69 polymerase for which the "open" and "closed" structures are known. Accordingly, an altered polymerase is provided which comprises or incorporates one, two, three, four, five or six amino acid substitution mutations to a different amino acid at the position or positions functionally equivalent to Lys790, Lys800, Arg806, Lys844, Lys874 and/or Lys878 in the RB69 DNA polymerase amino acid sequence. Preferably, the polymerase is a 9°N DNA polymerase comprising these analogous or functionally equivalent mutations. All combinations and permutations of one, two, three, four, five or six mutations are contemplated within the scope of the invention.

In terms of the nature of the different amino acid, the substitution mutation or mutations preferably convert the substituted amino acid to a non-basic amino acid (i.e. not lysine or arginine). Any non-basic amino acid may be chosen.

Preferred substitution mutation or mutations convert the substituted amino acid to an amino acid selected from:
 (i) acidic amino acids,
 (ii) aromatic amino acids, particularly tyrosine (Y) or phenylalanine (F); and
 (iii) non-polar amino acids, particularly, alanine (A), glycine (G) or methionine (M).

In one embodiment, the substitution mutation or mutations convert the substituted amino acid to alanine.

It should be noted that the present invention is not limited to polymerases which have only been altered in the above mentioned manner. Polymerases of the invention may include a number of additional mutations, such as for example the preferred mutant polymerases disclosed in detail in WO 2005/024010. In particular, a polymerase comprising substitution mutations at positions which are functionally equivalent to Leu408 and Tyr409 and Pro410 in the 9°N DNA polymerase amino acid sequence is contemplated. In a preferred embodiment, the polymerase is a 9°N DNA polymerase comprising the said substitution mutations.

In a specific embodiment, the polymerase comprises the substitution mutations which are functionally equivalent to at least one or two but preferably all of Leu408Tyr and Tyr409Ala and Pro410Val in the 9°N DNA polymerase amino acid sequence. In a preferred embodiment, the polymerase is a 9°N DNA polymerase comprising all the said substitution mutations.

The polymerase may further comprise a substitution mutation at the position functionally equivalent to Cys223 in the 9°N DNA polymerase amino acid sequence. In a preferred embodiment, the polymerase is a 9°N DNA polymerase comprising the said substitution mutation. In one embodiment, the polymerase comprises the substitution mutation functionally equivalent to Cys223Ser in the 9°N DNA polymerase amino acid sequence. In a preferred embodiment, the polymerase is a 9°N DNA polymerase comprising the said substitution mutation.

Preferably, the polymerase is a 9°N DNA polymerase comprising a combination of the above mentioned mutations.

The invention also relates to a 9°N polymerase molecule comprising, consisting essentially of or consisting of the amino acid sequence shown as any one of SEQ ID NO: 1, 3, 5 or 21. The invention also encompasses polymerases having amino acid sequences which differ from those shown as SEQ ID NOs: 1, 3, 5 and 21 only in amino acid changes which do not affect the function of the polymerase to a material extent. In this case the relevant function of the polymerase is defined as a reduced affinity for DNA such that the polymerase has an ability to incorporate a nucleotide or nucleotides into a plurality of separate DNA templates in each reaction cycle (compared to a control polymerase) and/or that the polymerase is capable of forming an increased number of productive polymerase-DNA complexes in each reaction cycle (compared to a control polymerase).

Thus, conservative substitutions at residues which are not important for this activity of the polymerase variants having reduced DNA affinity are included within the scope of the invention. The effect of further mutations on the function of the enzyme may be readily tested, for example using well known nucleotide incorporation assays (such as those described in the examples of WO 2005/024010 and in examples 3 and 4 below).

The altered polymerase of the invention may also be defined directly with reference to its reduced affinity for DNA, which together with a substantially unaltered fidelity and affinity for nucleotides produce the advantages associated with the polymerases of the invention. Thus, an altered polymerase is provided which has a dissociation constant ($K_D$) for DNA of at least, or in the region of between, approximately 2-fold greater, 3-fold greater, 4-fold greater or 5-fold greater than the unaltered control polymerase.

In one embodiment, an altered polymerase is provided which will dissociate from DNA in the presence of a salt solution, preferably a NaCl solution, having a concentration of less than or equal to about 500 mM, preferably less than 500 mM. The salt solution may be of a suitable concentration such that the reduced affinity polymerase of the invention can be distinguished from an unaltered polymerase which binds DNA more tightly. Suitable salt solution concentrations (preferably NaCl) are in the region of approximately 150 mM, 200 mM, 250 mM, 300 mM or 350 mM preferably 200 mM. Any suitable double stranded DNA molecule may be utilised to determine whether the alteration has the desired effect in terms of reducing DNA affinity. Preferably, the DNA molecule from which the polymerase dissociates comprises the sequence set forth as SEQ ID No.: 18. Preferably, at least approximately 40%, 50%, 60%, 70%, etc., of the polymerase will dissociate from the DNA at the relevant NaCl concentration in the wash solution.

Dissociation experiments may be carried out by any known means, such as, for example, by utilising the washing assay detailed in example 5 of the Experimental Section below (see also FIGS. 6 and 7).

As aforementioned, the reduction in DNA affinity is (preferably) achieved without a notable or significant decrease in the affinity of the polymerase for nucleotides. Surprisingly, the altered polymerase of the invention may also display comparable activity, for example, in terms of Vmax, to the unmodified polymerase even though the DNA binding affinity has been decreased. This surprising property displayed by the polymerases of the present invention is shown in the kinetic analysis of certain enzymes of the invention in particular in example 6 of the Experimental Section below and with reference to FIG. 8.

The altered polymerase of the invention may also be defined directly with reference to its improved ability to be purified from host cells in which the polymerase is expressed. Thus, thanks to the reduced affinity of the altered polymerase for DNA (which together with a substantially unaltered affinity for nucleotides and fidelity produce the advantages associated with the polymerases of the invention) the polymerase can more readily be purified. Less endogenous DNA from the host cell is co-purified during purification of the enzyme. Thus, a more pure product results since less endogenous DNA remains bound to the polymerase following the purification process. An additional advantage of the reduced affinity for DNA of the altered polymerases is that less severe purification procedures need to be utilised in order to provide a substantially pure polymerase preparation. Accordingly, less polymerase will be adversely affected by the purification process itself leading to a polymerase preparation with higher levels of overall activity. In addition, more uniform purification should be possible leading to less variability between batches of polymerase. Representative data regarding the improvement in carry over of endogenous DNA during the purification procedure is provided in Example 7 of the experimental section below.

Preferably, less than about 60 ng/ml, 50 ng/ml, 40 ng/ml, 30 ng/ml, 20 ng/ml, 10 ng/ml and more preferably less than about 5 ng/ml of host DNA is carried over following purification of the polymerase. Standard purification protocols may be utilised, such as for example see Colley et al., *J. Biol. Chem.* 264:17619-17622 (1989); *Guide to Protein Purification*, in *Methods in Enzymology*, vol. 182 (Deutscher, ed., 1990).

Thus, the invention provides an altered polymerase having an affinity for DNA such that;

(i) the polymerase has a dissociation constant for DNA of at least about, or approximately, 2-fold, 3-fold, 4-fold or 5-fold greater than the unaltered/control polymerase and/or (ii) at least 50%, 60%, 70% or 80% of the polymerase dissociates from DNA to which the polymerase is bound when a sodium chloride solution having a concentration of between about 200 nM and 500 nM, preferably between about 200 nM and 300 nM is applied thereto, and/or (iii) less than about 60, 50, 45, 40, 35, 30, 25, 20, 15, 10, 5, 3, 1 or 0.5 ng/ml of endogenous DNA remains bound to the polymerase following a purification process from the cell in which the polymerase is expressed; the alteration not significantly adversely affecting nucleotide binding ability or fidelity such that the polymerase is capable of;

(a) forming an increased number of productive polymerase-DNA complexes over a reaction cycle (giving improved levels of reaction completion), and/or (b) catalysing an improved (increased/elevated) overall level of nucleotide incorporation;
especially under conditions where the concentration of polymerase is limiting with respect to the concentration of DNA.

The invention further relates to nucleic acid molecules encoding the altered polymerase enzymes of the invention.

For any given altered polymerase which is a mutant version of a polymerase for which the amino acid sequence and preferably also the wild type nucleotide sequence encoding the polymerase is known, it is possible to obtain a nucleotide sequence encoding the mutant according to the basic principles of molecular biology. For example, given that the wild type nucleotide sequence encoding 9°N polymerase is known, it is possible to deduce a nucleotide sequence encoding any given mutant version of 9°N having one or more amino acid substitutions using the standard genetic code. Similarly, nucleotide sequences can readily be derived for mutant versions other polymerases from both family A and family B polymerases such as, for example, Vent™, Pfu, Tsp JDF-3, Taq, etc. Nucleic acid molecules having the required nucleotide sequence may then be constructed using standard molecular biology techniques known in the art.

In one particular embodiment the invention relates to nucleic acid molecules encoding mutant versions of the 9°N polymerase.

Therefore, the invention provides a nucleic acid molecule which encodes an altered 9°N polymerase, the nucleic acid molecule comprising, consisting essentially of or consisting of the nucleotide sequence of any of SEQ ID NO: 2, 4, 6, 19 or 20.

In accordance with the present invention, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Thus, there is provided an expression vector comprising, consisting essentially of or consisting of the nucleotide sequence of any of SEQ ID NO: 2, 4, 6, 19 or 20. Incorporation of cloned DNA into a suitable expression vector for subsequent transformation of said cell and subsequent selection of the transformed cells is well known to those skilled in the art as provided in Sambrook et al. (1989). Molecular cloning: A Laboratory Manual, Cold Spring Harbour Laboratory.

Such an expression vector includes a vector having a nucleic acid according to the invention operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the invention.

The nucleic acid molecule may encode a mature protein or a protein having a prosequence, including that encoding a leader sequence on the preprotein which is then cleaved by the host cell to form a mature protein.

The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Delgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase of the invention by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Preferred Uses of the Altered Polymerases

In a further aspect the invention relates to use of an altered polymerase having reduced affinity for DNA according to the invention for the incorporation of a nucleotide into a polynucleotide. As mentioned above, the nature of the nucleotide is not limiting since the altered polymerases of the invention retain affinity for the relevant nucleotides.

As aforementioned, the invention is based upon the realization that, the tight binding of a polymerase to the DNA template is not always an advantageous property. This is particularly the case in the context of sequencing reactions in which only a single nucleotide incorporation event is required in each reaction cycle for each template DNA molecule. In many of these sequencing reactions a labelled nucleotide is utilised.

Thus, the invention provides for use of a polymerase which has been altered such that it displays a reduced affinity for DNA and an ability to incorporate a labelled nucleotide into a plurality of separate DNA templates in each reaction cycle for incorporation of a labelled nucleotide into a polynucleotide, the label being utilised to determine the nature of the nucleotide added.

In one embodiment, the nucleotide comprises a ddNTP. Thus, the polymerase of the invention may be utilised in a conventional Sanger sequencing reaction, the details of which are well known in the art.

In a preferred embodiment, the nucleotide is a modified nucleotide which has been modified at the 3' sugar hydroxyl such that the substituent is larger in size than the naturally occurring 3' hydroxyl group.

The polymerases of the invention may be used in any area of technology where it is required/desirable to be able to incorporate nucleotides, for example modified nucleotides having a substituent at the 3' sugar hydroxyl position which is larger in size than the naturally occurring hydroxyl group, into a polynucleotide chain. They may be used in any area of technology where any of the desirable properties of the enzyme, for example improved rate of incorporation of nucleotides even under conditions where the DNA is present in excess and increased levels of reaction completion under these conditions, are required. This may be a practical, technical or economic advantage.

Although the altered polymerases exhibit desirable properties in relation to incorporation of modified nucleotides having a large 3' substituent due to their decreased affinity for DNA, the utility of the enzymes is not confined to incorporation of such nucleotide analogues. The desirable properties of the altered polymerase due to its reduced affinity for DNA may provide advantages in relation to incorporation of any other nucleotide, including unmodified nucleotides, relative to enzymes known in the art. In essence, the altered polymerases of the invention may be used to incorporate any type of nucleotide that they have the ability to incorporate.

The polymerases of the present invention are useful in a variety of techniques requiring incorporation of a nucleotide into a polynucleotide, which include sequencing reactions, polynucleotide synthesis, nucleic acid amplification, nucleic acid hybridisation assays, single nucleotide polymorphism studies, and other such techniques. Use in sequencing reactions represents a most preferred embodiment. All such uses and methods utilizing the modified polymerases of the invention are included within the scope of the present invention.

The invention also relates to a method for incorporating nucleotides into DNA comprising allowing the following components to interact:
 (i) A polymerase according to the invention;
 (ii) a DNA template; and
 (iii) a nucleotide solution.

As discussed above, the polymerase of the invention has particular applicability in reactions where incorporation of only a single or relatively few nucleotides are required in each reaction cycle. Often in these reactions one or more of the nucleotides will be labelled. Accordingly, the invention provides a method for incorporating labelled nucleotides into DNA comprising allowing the following components to interact:
 (i) A polymerase which has been altered such that it displays a reduced affinity for DNA and an ability to incorporate a labelled nucleotide into a plurality of separate DNA templates in each reaction cycle.
 (ii) a DNA template; and
 (iii) a nucleotide solution.

In one specific embodiment, the invention provides a method for incorporating nucleotides which have been modified at the 3' sugar hydroxyl such that the substituent is larger in size than the naturally occurring 3' hydroxyl group into DNA comprising allowing the following components to interact:
 A polymerase according to the present invention (as described above)
 a DNA template; and
 a nucleotide solution containing the nucleotides which have been modified at the 3' sugar hydroxyl such that the substituent is larger in size than the naturally occurring 3' hydroxyl group.

Particularly preferred are uses and methods carried out on a clustered array. Clustered arrays of nucleic acid molecules may be produced using techniques generally known in the art. By way of example, WO 98/44151 and WO 00/18957 (both of which are incorporated by reference herein) both describe methods of nucleic acid amplification which allow amplification products to be immobilised on a solid support in order to form arrays comprised of clusters or "colonies" of immobilised nucleic acid molecules. Reference is also made to WO 2005/078130 including the citations referred to therein, the contents of all of which are hereby incorporated by reference. Incorporation on clusters, in particular sequencing on clustered arrays, provides specific advantages because the polymerase is able to incorporate nucleotides into multiple DNA templates located in close proximity, thus providing a highly efficient reaction.

The above components are allowed to interact under conditions which permit the formation of a phosphodiester linkage between the 5' phosphate group of a nucleotide and a free 3' hydroxyl group on the DNA template, whereby the nucleotide is incorporated into a polynucleotide. Preferred nucleotides, including modified nucleotides, are described in detail above.

The incorporation reactions may occur in free solution or the DNA templates may be fixed to a solid support.

The rate of incorporation of the nucleotide exhibited by a mutant enzyme may be similar to the rate of incorporation of nucleotides exhibited by the unaltered enzyme. Due to the improved activity of the modified enzyme, thanks to its reduced affinity for DNA, the same rate of incorporation combined with the ability to incorporate nucleotides into a plurality of templates in a single reaction cycle improves the overall rates of completion. However, it is not necessary for the rate of incorporation of nucleotides to be precisely the same to that of the unaltered enzyme for a mutant enzyme to be of practical use. The rate of incorporation may be less than, equal to or greater than the rate of incorporation of nucleotides by the unaltered enzyme, provided the overall reaction efficiency in terms of reaction completion is improved.

In one particular embodiment of the invention, the altered polymerases of the invention may be used to incorporate modified nucleotides into a polynucleotide chain in the context of a sequencing-by-synthesis protocol. In this particular aspect of the method the nucleotides may have been modified at the 3' sugar hydroxyl such that the substituent is larger in size than the naturally occurring 3' hydroxyl group. These nucleotides are detected in order to determine the sequence of a DNA template.

Thus, in a still further aspect, the invention provides a method of sequencing DNA comprising allowing the following components to interact:
  A polymerase according to the present invention (as described above)
  a DNA template; and
  a nucleotide solution containing the nucleotides which have been modified at the 3' sugar hydroxyl such that the substituent is larger in size than the naturally occurring 3' hydroxyl group
  followed by detection of the incorporated modified nucleotides thus allowing sequencing of the DNA template.

The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g. a short oligonucleotide) which hybridises to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added will be determined, thus providing sequence information for the DNA template.

Such DNA sequencing may be possible if the modified nucleotides can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

In a preferred embodiment the modified nucleotides carry a label to facilitate their detection. Preferably this is a fluorescent label. Each nucleotide type may carry a different fluorescent label. However the detectable label need not be a fluorescent label. Any label can be used which allows the detection of the incorporation of the nucleotide into the DNA sequence.

One method for detecting the fluorescently labelled nucleotides, suitable for use in the methods of the invention, comprises using laser light of a wavelength specific for the labelled nucleotides, or the use of other suitable sources of illumination.

In one embodiment, the fluorescence from the label on the nucleotide may be detected by a CCD camera.

If the DNA templates are immobilised on a surface they may preferably be immobilised on a surface to form a high density array, which is preferably a clustered or "colonial" array as discussed supra. In one embodiment, and in accordance with the technology developed by the applicants for the present invention, the high density array comprises a single molecule array, wherein there is a single DNA molecule at each discrete site that is detectable on the array. Single-molecule arrays comprised of nucleic acid molecules that are individually resolvable by optical means and the use of such arrays in sequencing are described, for example, in WO 00/06770, the contents of which are incorporated herein by reference. Single molecule arrays comprised of individually resolvable nucleic acid molecules including a hairpin loop structure are described in WO 01/57248, the contents of which are also incorporated herein by reference. The polymerases of the invention are suitable for use in conjunction with single molecule arrays prepared according to the disclosures of WO 00/06770 of WO 01/57248. However, it is to be understood that the scope of the invention is not intended to be limited to the use of the polymerases in connection with single molecule arrays.

Single molecule array-based sequencing methods may work by adding fluorescently labelled modified nucleotides and an altered polymerase to the single molecule array. Complementary nucleotides base-pair to the first base of each nucleotide fragment and are then added to the primer in a reaction catalysed by the improved polymerase enzyme. Remaining free nucleotides are removed.

Then, laser light of a specific wavelength for each modified nucleotide excites the appropriate label on the incorporated modified nucleotides, leading to the fluorescence of the label. This fluorescence may be detected by a suitable CCD camera that can scan the entire array to identify the incorporated modified nucleotides on each fragment. Thus millions of sites may potentially be detected in parallel. Fluorescence may then be removed.

The identity of the incorporated modified nucleotide reveals the identity of the base in the sample sequence to which it is paired. The cycle of incorporation, detection and identification may then be repeated approximately 25 times to determine the first 25 bases in each oligonucleotide fragment attached to the array, which is detectable.

Thus, by simultaneously sequencing all molecules on the array, which are detectable, the first 25 bases for the hundreds of millions of oligonucleotide fragments attached in single copy to the array may be determined. Obviously the invention is not limited to sequencing 25 bases. Many more or less bases may be sequenced depending on the level of detail of sequence information required and the complexity of the array.

Using a suitable bioinformatics program the generated sequences may be aligned and compared to specific reference sequences. This allows determination of any number of known and unknown genetic variations such as single nucleotide polymorphisms (SNPs) for example.

The utility of the altered polymerases of the invention is not limited to sequencing applications using single-molecule arrays. The polymerases may be used in conjunction with any type of array-based (and particularly any high density array-based) sequencing technology requiring the use of a polymerase to incorporate nucleotides into a polynucleotide chain, and in particular any array-based sequencing technology which relies on the incorporation of modified nucleotides having large 3' substituents (larger than natural hydroxyl group), such as 3' blocking groups.

The polymerases of the invention may be used for nucleic acid sequencing on essentially any type of array formed by immobilisation of nucleic acid molecules on a solid support. In addition to single molecule arrays suitable arrays may include, for example, multi-polynucleotide or clustered arrays in which distinct regions on the array comprise multiple copies of one individual polynucleotide molecule or even multiple copies of a small number of different polynucleotide molecules (e.g. multiple copies of two complementary nucleic acid strands).

In particular, the polymerases of the invention may be utilised in the nucleic acid sequencing method described in WO 98/44152, the contents of which are incorporated herein by reference. This International application describes a method of parallel sequencing of multiple templates located at distinct locations on a solid support. The method relies on incorporation of labelled nucleotides into a polynucleotide chain.

The polymerases of the invention may be used in the method described in International Application WO 00/18957, the contents of which are incorporated herein by reference. This application describes a method of solid-phase nucleic acid amplification and sequencing in which a large number of distinct nucleic acid molecules are arrayed and amplified simultaneously at high density via formation of nucleic acid colonies and the nucleic acid colonies are subsequently sequenced. The altered polymerases of the invention may be utilised in the sequencing step of this method.

Multi-polynucleotide or clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. The contents of WO 98/44151 and WO 00/18957 relating to the preparation of clustered arrays and use of such arrays as templates for nucleic acid sequencing are incorporated herein by reference. The nucleic acid molecules present on the clustered arrays prepared according to these methods are suitable templates for sequencing using the polymerases of the invention. However, the invention is not intended to be limited to use of the polymerases in sequencing reactions carried out on clustered arrays prepared according to these specific methods.

The polymerases of the invention may further be used in methods of fluorescent in situ sequencing, such as that described by Mitra et al. Analytical Biochemistry 320, 55-65, 2003.

The present invention also contemplates kits which include the polymerase of the invention, possibly packaged together with suitable instructions for use. The polymerase will be provided in a form suitable for use, for example provided in a suitable buffer or may be in a form which can be reconstituted for use (e.g. in a lyophilized form).

Thus, a kit is provided for use in a nucleotide incorporation reaction or assay comprising a polymerase of the invention as described herein and a solution of nucleotides, the nucleotides being such that the polymerase can incorporate them into a growing DNA strand. Preferred nucleotides include suitably labelled nucleotides which can thus be used in sequencing reactions for example. Labels may include fluorescent labels, radiolabels and/or mass labels as are known in the art.

In one preferred embodiment, the nucleotide solution comprises, consists essentially of or consists of synthetic (i.e. non-natural) nucleotides such as ddNTPs for example. The kit may thus be utilised in a Sanger sequencing reaction for example.

In a further embodiment, the nucleotide solution comprises, consists essentially of or consists of modified nucleotides. Preferred modified nucleotides are defined above with respect to the polymerases of the invention and this description applies mutatis mutandis here.

The kit may, in a further embodiment, also incorporate suitable primer and/or DNA template molecules which allow a nucleotide incorporation reaction to be carried out.

In a still further aspect, the invention provides a method for producing a polymerase according to the invention comprising:
(i) selecting residues for mutagensis in the polymerase;
(ii) producing a mutant polymerase in accordance with the selection made in (i);
(iii) determining the affinity of the mutant polymerase for DNA; and
(iv) if the affinity for DNA is reduced, testing the polymerase for an ability to form an increased number of productive polymerase-DNA complexes in each reaction cycle.

Preferably affinity for nucleotides is unaffected, but may be considered satisfactory if it remains of the same order as for the unmodified polymerase.

In one embodiment, the method further comprises ensuring that the fidelity of the polymerase remains of the same order following mutagenesis.

Preferably fidelity is unaffected, but may be considered acceptable if it remains of the same order as for the modified polymerase.

Reaction cycle is as defined above.

In a preferred embodiment, the test of the polymerase includes the use of synthetic nucleotides to determine whether an increased number of productive polymerase-DNA complexes are being formed. Suitable nucleotide incorporation assays in which the polymerase may be tested are known in the art (e.g. see WO2005/024010) and are described in more detail in the experimental section below.

In one embodiment, residues are selected on the basis of the 9°N primary amino acid sequence. In one embodiment, the selection is made by predicting which amino acids will contact the DNA. Alternatively, residues may be selected which are predicted to stabilise the interaction of the polymerase with DNA and/or which are found in the DNA binding domain of the polymerase and/or which are basic. Predictions may be based on crystal structures of a suitable polymerase, as discussed supra and in the experimental section (example 1).

Methods of mutagenesis, in particular site-directed mutagenesis, are well characterised in the art and kits are commercially available. Accordingly, these techniques are not discussed in detail. Any suitable technique may be utilized in the method of the invention.

The reduction in affinity for DNA may be measured by any suitable method. Preferably, the affinity is reduced at least, or approximately, 1.5-fold, 2-fold, 3-fold, 4-fold or 5-fold etc. compared to the original unaltered polymerase. This affinity may be measured with reference to the dissociation constant for example.

In a preferred embodiment, the polymerase is a family B polymerase, preferably derived from a thermophilic archaeon and most preferably is 9°N polymerase.

BRIEF DESCRIPTION OF THE DRAWINGS

The invention will be further understood with reference to the following experimental section and figures in which:

FIG. 9 presents the nucleotide and amino acid sequences encoded by the codon-modified gene of clone 9

ABBREVIATIONS

Figure 1A:
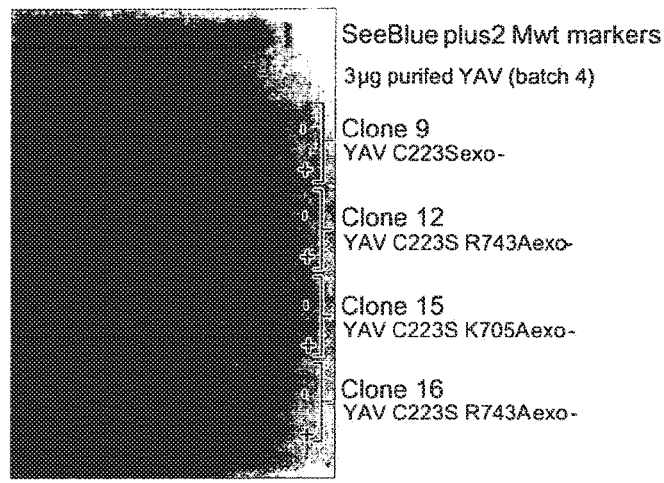
FIGS. 1A and 1B show overexpression of mutant enzymes of the invention.

MW—Molecular Weight; PM—protein marker; cl 9—clone 9.

DETAILED DESCRIPTION OF THE INVENTION

Experimental Section

Example 1—Preparation of Altered Polymerases

Rationale

Site-directed mutations were introduced in the C-terminal region of 9°N-7 YAV C223S polymerase in an attempt to reduce the affinity of the enzyme for DNA (wild-type 9°N-7 polymerase has a very high affinity for DNA, Kd=50 pM; Southworth et al. 1996. PNAS. 93, 5281).

An energy minimised overlaid alignment (contracted by Cresset) of the crystal structures of the open form of 9°N-7 DNA polymerase (PDB=1qht), the open structure of a closely related DNA polymerase RB69 (PDB=1ih7) and the closed form of RB69 (PDB=1ig9) was used as a structural model for the identification of key residues involved in DNA binding. The crystal structure of the closed form of RB69 polymerase (Franklin et al. 2001. Cell 105, 657) identified a number of residues that formed H-bond or electrostatic interactions with the complexed DNA, either directly to the nucleotide bases or the phosphate backbone. A high proportion of these residues were basic (Lys790, 800, 844, 874, 878 and Arg806), consistent with their likely interaction with acidic phosphate groups. Inspection of the closed RB69 structure showed that the majority of these residues adopted orientations toward the bound duplex. No analogous structure for the closed form of 9°N-7 pol exists and so we used our structural alignment to identify basic residues in the open form of 9°N-7 pol which adopted analogous conformations to the basic residues (of those above) from the RB69 open structure. Of the 6 basic residues from RB69, 3 were found to have a corresponding basic residue in 9°N-7, these were: Arg743 (RB69 Lys878), Arg713 (Lys800) and Lys705 (Lys844). It was decided to engineer 4 mutant enzymes, the alanine variants of the residues shown (R743A, R713A and K705A) and a 71 amino acid deletion (71), which removed an α-helix from the thumb subdomain (residues disordered in the 9°N-7 pol structure) within which the three residues above were located.

Mutagenesis and Cloning

Mutations were introduced into pSV19 (plasmid encoding 9°N-7 YAV C223S exo-polymerase) via a PCR method using Stratagene Quikchange XL kit and the protocol thereof (also see WO 2005/024010)

Mutagenic primers used:

```
R743A.
fwd
                                     (SEQ ID NO: 9)
5'-CCCGGCGGTGGAGGCGATTCTAAAAGCC-3' rev
                                    (SEQ ID NO: 10)
3'-GGGCCGCCACCTCCGCTAAGATTTTCGG-5'

R713A
fwd
                                    (SEQ ID NO: 11)
5'-GAAGGATAGGCGACGCGGCGATTCCAGCTG-3' rev
                                    (SEQ ID NO: 12)
3'-CTTCCTATCCGCTGCGCCGCTAAGGTCGAC-5'

K705A
fwd
                                    (SEQ ID NO: 13)
5'-GCTACATCGTCCTAGCGGGCTCTGGAAGG-3' rev
                                    (SEQ ID NO: 14)
3'-CGATGTAGCAGGATCGCCCGAGACCTTCC-5'

71 (C-terminus 704)
fwd
                                    (SEQ ID NO: 15)
5'-GCTACATCGTCCTATGAGGCTCTGGAAGG-3' rev
                                    (SEQ ID NO: 16)
3'-CGATGTAGCAGGATACTCCGAGACCTTCC-5'
```

Figure 1B:
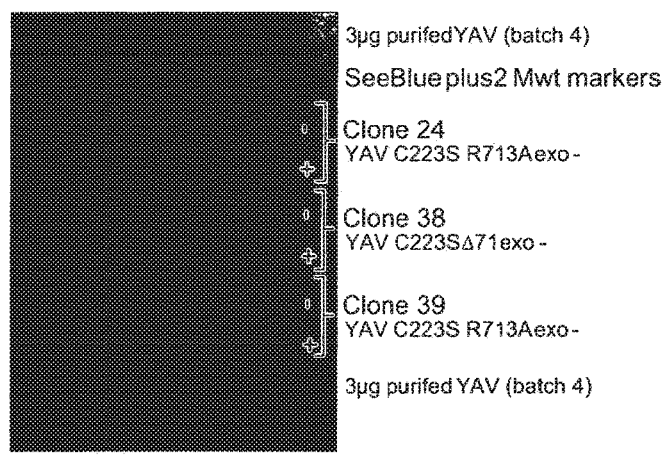

Potential clones were selected and PCR fragments of the gene sequenced to confirm the presence of the mutation. Positive clones were produced for all mutants.
Overexpression and Growth:
  Transformed into expression strain Novagen RosettaBlue DE3 pLysS
  Growth and induction carried out as described in Experimental section of WO 2005/024010.
  Harvest and lysis carried out as described in Experimental section of WO 2005/024010.
  Purification carried out as described in Experimental section of WO 2005/024010.
Results:
Successful overexpression of mutant enzymes was achieved. All mutant enzymes were overexpressed. SDS-PAGE gels were run to check overexpression of the constructs (−=uninduced; +=IPTG induced). The resulting gels are shown in FIG. 1.

Example 2—NUNC Tube Assay Using Crude Protein Preparation

Small 5 ml cultures of the mutant enzymes (along with a culture of YAV C223S exo- for direct comparison) were taken through a quick purification as outlined in WO 2005/024010 up until the heat treatment step. At this point, the samples were considered to be sufficiently pure to test their activity.

The buffers for each of the crude preparations were exchanged into enzymology buffer (50 mM Tris pH 8.0, 6 mM MgSO4, 1 mM EDPA, 0.05% Tween20) using an S300 gel filtration spin-column. The samples were not normalised for concentration. The test employed was a simple incorporation of ffTTP into surface-coupled A-template hairpin. 2 pmoles of 5'-amino oligo 815 (5'-CGATCACGATCACGAT-CACGATCACACGATCACGATCACGCTGATGTGCAT-GCTTG TTTTTTTACAACAGCATGCACATCAGCG-3') (SEQ ID NO: 17) was coupled to a NUNC-nucleolink strip according to the manufacturers protocol.

Once washed, each well was incubated with a 20 □l aliquot of a crude enzyme preparation (identity of enzyme listed below) and 5 □M ffT-N3-647. The strip was then incubated at 45° C. for 30 minutes. The experiment was performed in duplicate. Upon completion of the 30 minute incubation, wells were washed with 3×100 □l of high salt wash buffer (10 mM Tris pH 8.0, 1M NaCl, 10 mM EDTA) and then 3×100 □l of MilliQ water. Strips were scanned on a typhoon fluorescence imager CY5 filter, PMT=450 V).

Figure 2:
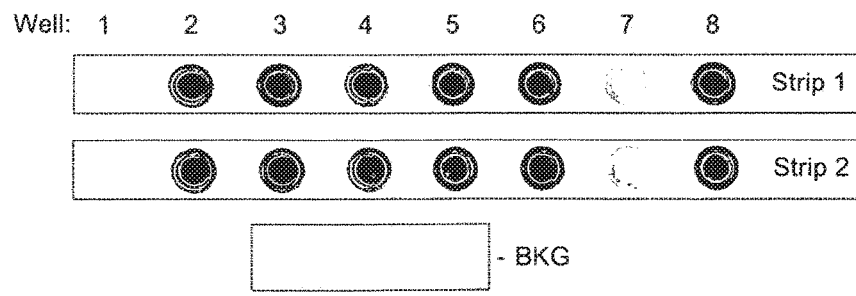
FIG. 2 shows results of a NUNC tube assay using crude preparations of the mutant enzymes.

The results are presented in FIG. 2, in which the wells are as follows:
1=20 µl enzymology buffer only+1 µl 100 µM ffT-N3-647
2-20 µl crude YAV C223S exo-+1 µl 100 µM ffT-N3-647
3=20 µl crude YAV C223S R743A exo- (clone 12)+1 µl 100 µM ffT-N3-647
4=20 µl crude YAV C223S K705A exo- (clone 15)+1 µl 100 µM ffT-N3-647
5=20 µl crude YAV C223S R743A exo- (clone 16)+1 µl 100 µM ffT-N3-647
6=20 µl crude YAV C223S R713A exo- (clone 24)+1 µl 100 µM ffT-N3-647
7-20 µl crude YAV C223S 71 exo- (clone 38)+1 µl 100 µM ffT-N3-647
8=20 µl crude YAV C223S R713A exo- (clone 39)+1 µl 100 µM ffT-N3-647
Results
Enzymology was observed in all wells except the background wells (MilliQ only) and well 1 (no enzyme control).

The fluorescence density is proportional to the amount of ffTTP incorporation—the darker the well, the greater the level of incorporation. Performance of the mutant enzymes will be discussed relative to YAV (clone 9)(YAV C223S exo-). Deletion of the tip of the thumb subdomain (71 mutant) results in an enzyme that is severely catalytically compromised, and only incorporates to 35% of the level seen for clone 9. Mutant K705A was equivalent to clone 9. The two arginine mutants R743A and R713A showed elevated levels of incorporation, showing ~45% improvements over clone 9.
Conclusion Mutant enzymes K705A, R713A and R743A display improved levels of incorporation and decreased affinity of the enzyme for DNA. Removal of all three of these basic residues, in combination with deletion of additional residues, abolishes activity (71 mutant). It may be that substitution of all three residues would not lead to a decrease in activity, in the absence of further mutations/deletions.

Example 3—Signal Base Incorporation Assay

Figure 3A:
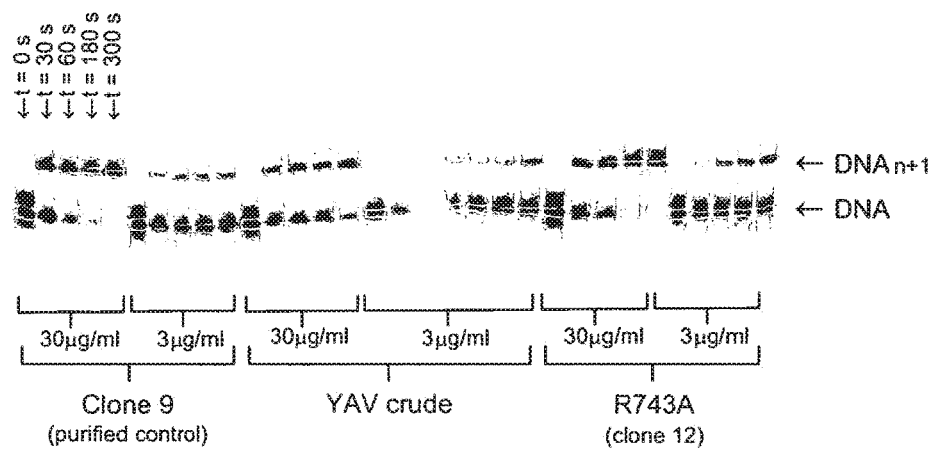
FIGS. 3A and 3B show results of a single base incorporation assay utilising the mutant enzymes.
Figure 3B:
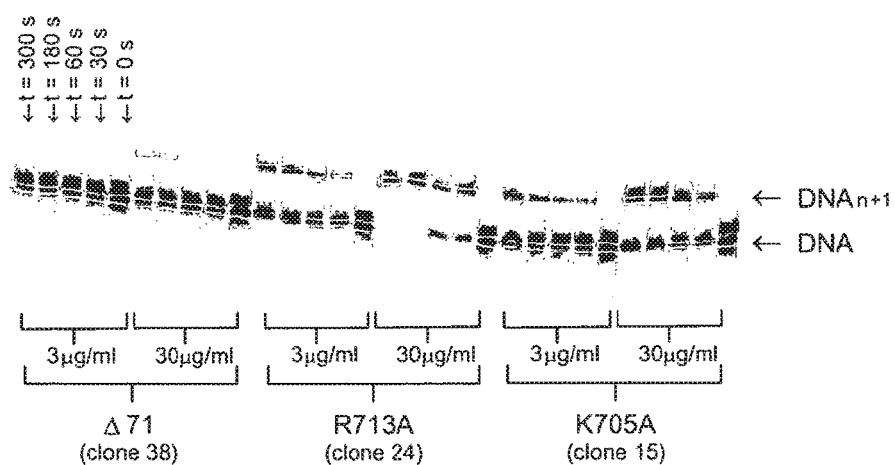

The activity of the crude enzyme preparations (normalised concentrations) was measured using the single base incorporation assay as described in WO 2005/024010. 10 minute incubations were run with either 30 or 3 µg/ml crude enzyme preparation in the presence of 2 µM ffT-N3-cy3 and 20 nM 10A hairpin DNA ($^{32}$P-labelled), aliquots of the reaction mixture were withdrawn at 0, 30, 60, 180 and 600 s and run on a 12% acrylamide gel.
Results The gel images are shown in FIG. 3.

Figure 4:
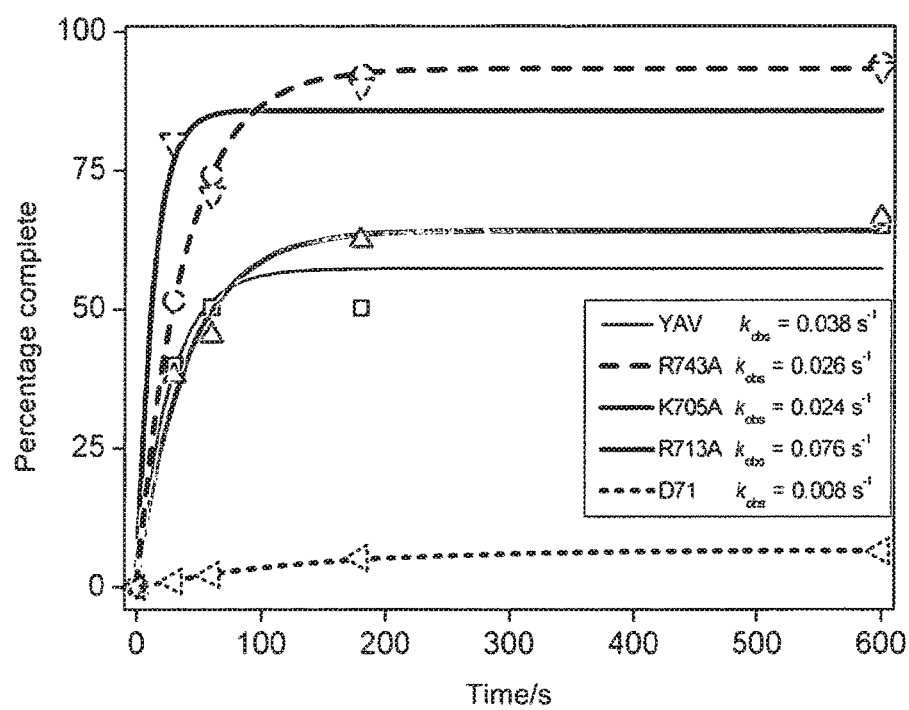
FIG. 4 is a further presentation of the activity of the mutant enzymes.

The band intensities were quantified using Imagequant and the fluorescence intensity plotted versus incubation time to generate the time-courses shown in FIG. 4.

These data give an estimate of the performance of the mutant enzymes for the first base incorporation of ffTTP relative to YAV. Due to the concentration normalisation, the activities are directly comparable. The 71 mutant is essentially inactive (kobs is 21% of that observed for YAV), R743A and K705A have comparable activities to YAV, but R713A shows a significant enhancement in both kobs (2× that observed for YAV) and the level of cycle completion.

Example 4—Single Base Incorporation Assay for Purified Polymerases Under Conditions where [DNA] is Greater than [Pol]

Figure 5:
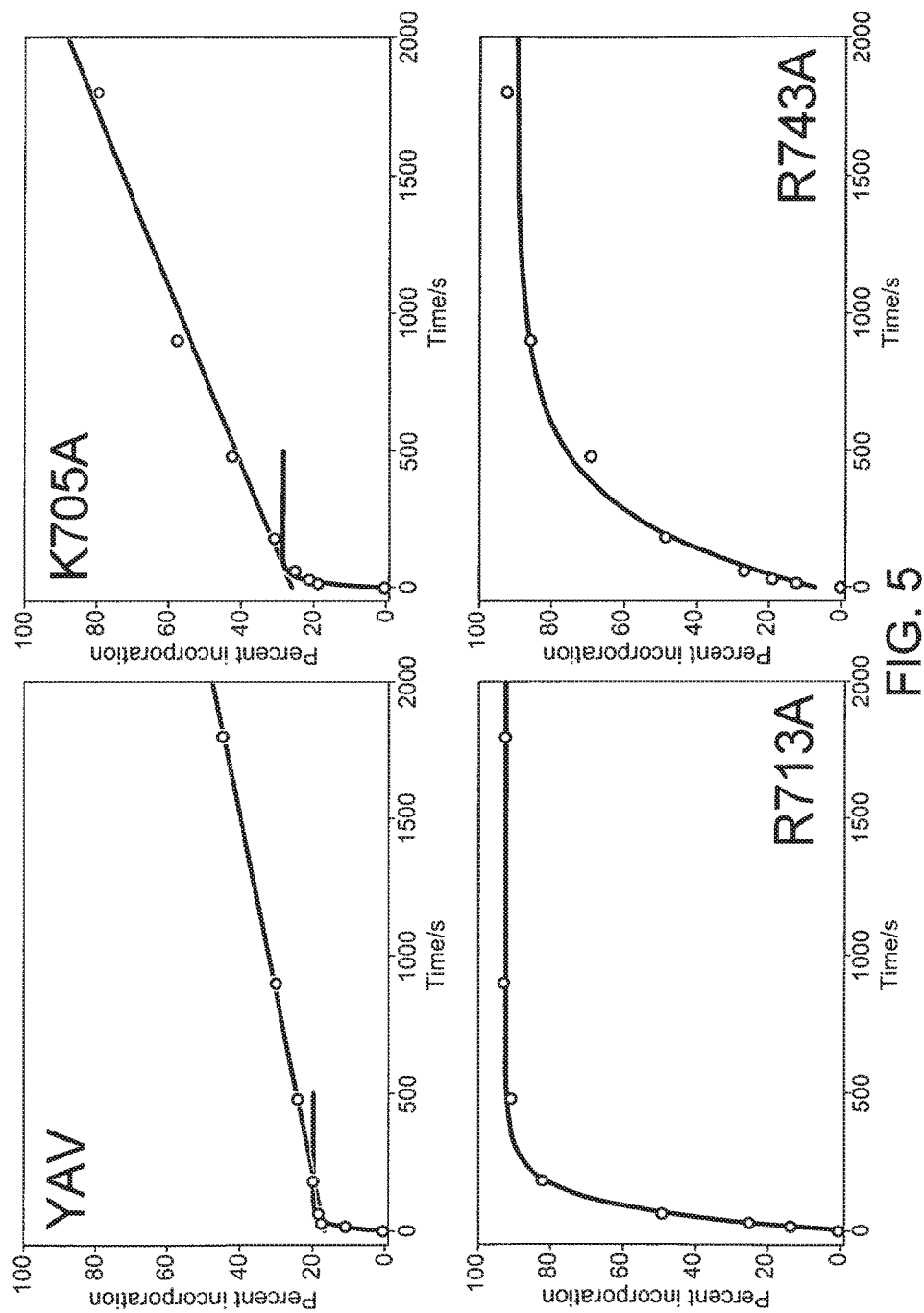
FIG. 5 presents results of timecourses for a single base incorporation assay at [DNA]>[pol] (ratio 5:1) for the control polymerase (YAV) and for each of the three mutant enzymes (K705A, R713A and R743A).

The activity of the purified enzyme preparations of Clone 9 polymerase (YAV C223S exo-) and the thumb sub-domain mutants K705A, R713A and R743A was measured using the single base incorporation assay as described in WO 2005/024010. The experiment was carried out such that the respective concentrations of DNA and polymerase were at a ratio of approximately 5:1. Thus, the ability of the enzyme to incorporate nucleotides into multiple DNA template molecules in a single reaction cycle was investigated. 30 minute incubations were run with 4 nM purified enzyme in the presence of 20 nM 10A hairpin DNA ($^{32}$P-labelled) and 2 µM ffT-N3-cy3, aliquots of the reaction mixture were withdrawn at 0, 15, 30, 60, 180, 480, 900 and 1800 s intervals and run on a 12% acrylamide gel.
Results The band intensities were quantified using Imagequant and the fluorescence intensity, converted into percentage completion (based on the relative intensities of the starting material and final product bands on the gel) plotted versus incubation time to generate the timecourses shown in FIG. 5.

Timecourse plots for clone 9 and K705A are biphasic in nature, displaying an initial exponential "burst" phase (black line) followed by a linear dependence of product conversion with time (grey line). The amplitude of the burst phase is greater for K705A than for clone 9 (~28% and 19% respectively) and the gradient of the linear phase is steeper (hence faster) for K705A than clone 9. The significance of this observation is discussed below.

In contrast to this, both R713A and R743A mutant enzymes do not show this biphasic nature, instead, only the fast exponential phase is observed. In both cases, the amplitude of the exponential phase is ~90% indicating a higher degree of product conversion within this exponential phase than either clone 9 or K705A. The burst phase equates to the rate of incorporation of ffTTP of the population of DNA molecules associated with a polymerase prior to reaction initiation i.e. maximum rate at which the ternary pol:DNA:ffTTP complex can turnover. Any subsequent phase is attributed to a slower dissociation/re-association process required for the polymerase to sequester new substrate molecules (DNA and ffTTP). The biphasic nature observed for clone 9 and K705A suggests that the slow post-burst phase is caused by the difficulty of the enzyme to dissociate and re-associate with DNA, most likely due to their low Kd (DNA).

The mutation of basic residues that may contact duplex DNA when bound by the polymerase (namely R713 and R743) to remove this functionality results in mutant enzymes which only display burst kinetics (R713A and R743A). We interperet this in one of two ways, i) as having improved the enzymes ability to dissociate and re-associate with DNA by decreasing the affinity for DNA (increased Kd(DNA)) and/or ii) the decrease in affinity for DNA in these mutants results in a larger "active enzyme" fraction in the polymerase preparation. It has been shown that impure DNA polymerase (contaminated with $E.$ $coli$ genomic DNA carried through from lysis) inhibits the enzyme by reducing the active enzyme fraction of the preparation.

The crude fitting of the timecourses suggests that the observed rate constants for the burst phase seen for clone 9 and K705A are comparable (kobs~0.06 s-1) whereas this rate constant is smaller for R713A (kobs~0.01 s-1) and R743A (kobs~0.004 s-1). Under these experimental conditions, the burst is faster for clone 9 and K705A than for R713A or R743A, but the latter two enzymes reach completion in a shorter period of time due to the absence of the slow, linear dissociation/re-association phase inherent to clone 9 and K705A.

Example 5—Ashing Assay

Employing a washing assay qualitatively assesses the affinity of purified enzyme preparations for DNA. 4 (1×8) NUNC nucleolink strips were functionalized with 2 pmoles of 5'-amino A-template hairpin, oligo 815 (5' H2N-CGATCACGATCACGATCACGATCACGATCACGATCACGCTGATGTGCATGCGACAACAGC ATGCACATCAGCG-3') (SEQ ID NO: 18) according to the manufacturer's protocol.

Once washed, each well was incubated with a 20 μl aliquot of 500 nM enzyme (clone 9, K705A, R713A or R743A mutants) at 45° C. for 30 minutes. Post incubation, each well was washed with 3×100 ml of 10 mM Tris pH 8.0, 10 mM EDTA including varying concentrations of NaCl (0, 0.05, 0.1, 0.3, 0.4, 0.75, 1.0, 2.0 M) and then 3×100 ml MilliQ water. Wells were subsequently pre-equilibrated with enzymology buffer prior to a further incubation of 20 μl of 2 μM ffT-N3-647 at 45° C. for 30 minutes. Wells were washed with 3×100 ml high salt wash buffer (10 mM Tris pH 8.0, 1M NaCl, 10 mM EDTA) and then 3×100 ml MilliQ water. Strips scanned on Typhoon fluorescence imager (y5 filter, PMT=500 V).

Results

Figure 6:
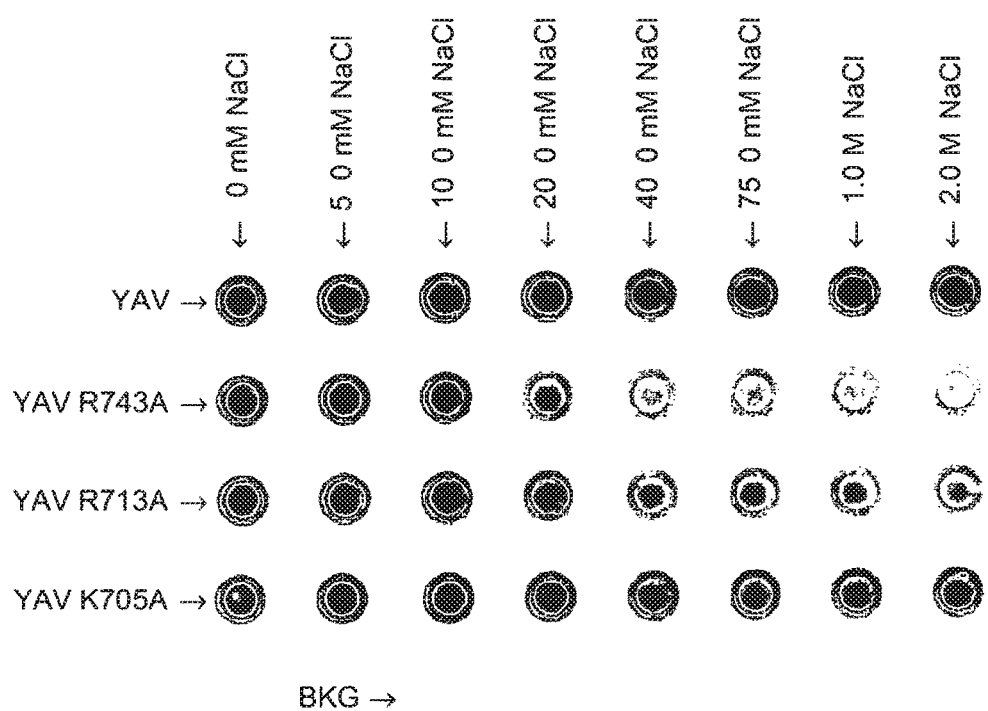
FIG. 6 shows results of the washing assay, with the fluorescence image of the NUNC wells shown.

The fluorescence image of the NUNC wells is shown in FIG. 6.

Any fluorescence in the wells is due to residual enzyme bound to the surface-coupled DNA post-wash. Increasing the ionic strength of the wash buffer between incubation should destabilise the interaction between the polymerase and the DNA by masking electrostatic interactions. Enzyme should be more effectively washed off the DNA at higher ionic strength.

Figure 7:
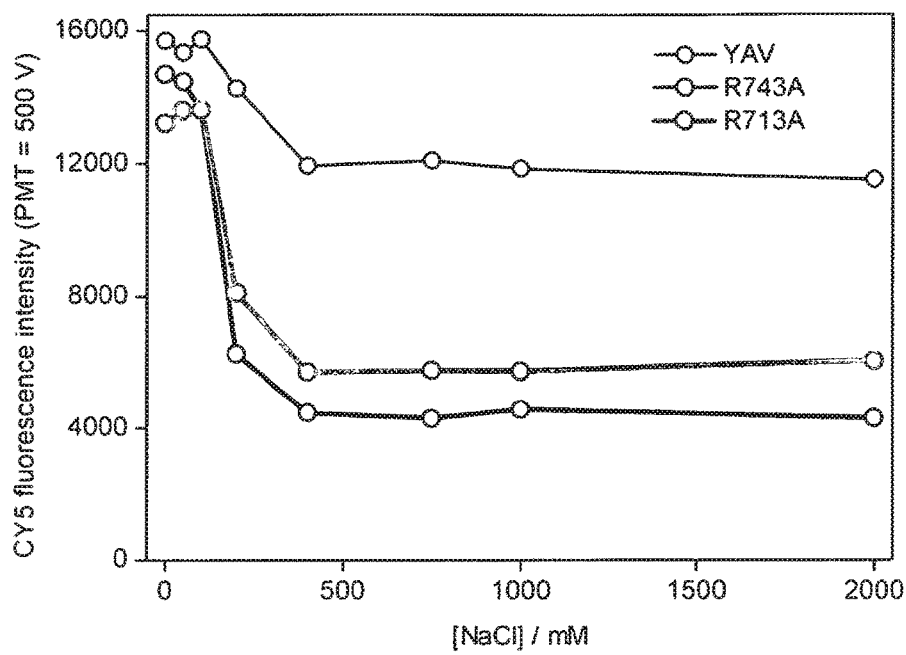
FIG. 7 also presents results of the washing assay, showing the affinity of the respective polymerases for a DNA template (the data for K705A has been omitted for clarity).

When a low ionic strength wash is employed between incubations all enzymes tested displayed a high level of incorporation, therefore ineffective at dissociating enzyme from DNA. As the concentration of NaCl in the wash buffer increased, the behaviour of the enzymes relative to each other changed. Mutant enzymes R713A and R743A were more effectively removed from the DNA at (NaCl)<200 mM, whereas K705A and clone 9 showed a similar response to each other, but required higher (NaCl) to remove them from the DNA. Even after a wash with 2 M NaCl, a significant (ca. 75%) level of incorporation relative to a 0 M NaCl wash was observed for clone 9. This is clearly illustrated in the plot shown in FIG. 7 (the data for K705A has been omitted for clarity). Interestingly, none of the enzymes tested appeared to be completely removed from the DNA after experiencing a 2 M NaCl wash.

From this experiment, it is clear that mutating residues R713 and R743 result in enzymes that display lower affinity for DNA than clone 9, as evidenced by their ability to be washed from DNA by lower ionic strength washes.

Example 6—Incorporatioc Kinetics of ffT-N3-Cy3 by Clone 9, R713A and R743A

The kinetic characterization of the enzymes was conducted using NUNC tube assay and involved the measurement of rate constants for the first order incorporation of ffT N3 cy3 where [DNA]<<[pol] or [ffNTP], at a variety of [ffTTP]. Below is described the methodology used for each of the three polymerases tested.

Six (1×8) NUNC nucleolink strips were functionalized with 2 pmoles of 5'-amino A template hairpin oligo 815 (5' H2N-CGACACGATCACGATCACGCGATGTGCATGCT-GTTGTTTTTTTACAACAGC ATGCACATCAGCG-3') (SEQ ID NO: 18), according to the manufacturer's protocol.

Each strip was employed for a time-course experiment at a particular (ffT-N3-cy3). 20 μl of enzymology buffer (50 mM Tris pH 8.0, 6 mM MgSO4, 1 mM EDTA, 0.05% Tween20) was incubated in each NUNC well at 45° C. for 2 minutes.

Time-courses were initiated by addition of a 20 μl aliquot of 2× enzymology mix (X μM ffT-N3-cy3, 1.1 μM polymerase in enzymology buffer) pre-equilibrated at 45° C. for 2 minutes using an 8-channel multipipette in order to start reactions in individual wells at identical time-points. The action of adding the 2× enzymology mix to the buffer in the well is sufficient to allow adequate mixing. The reactions were stopped at desired time-points by the addition of 125 μl of 250 mM EDTA. After reactions in all 8 wells stopped, strips were washed with 3×100 ml high salt wash (10 mM Tris pH 8.0, 1 M NaCl, 10 mM EDTA) and then 3×100 ml MilliQ water and then scanned on a Typhoon fluorescence imager (Cy3 filter, PMT=500 V). Fluorescence intensities in each well were quantified using Imagequant. Plotting the variation in Cy3 fluorescence intensity vs. time generates time-course graphs. Under our experimental conditions, these time-course plots evaluate well to a single exponential decay process (fitted to equation: y=yo+Aexp (x/t)) from which the reaction half life, t, is determined, the inverse of which is termed the observed rate constant kobs (kobs=1/t).

The magnitude of the observed rate constant is dependent on the concentration of ffT-N3-cy3, so by repeating this experiment at different ffT-N3-cy3 concentrations a range of kobs values can be determined for a particular enzyme. The variation of kobs with ffT-N3-cy3 concentration is hyperbolic and fits well to the Michealis-Menten equation: VMax=(kpolx[S])/(Kd+[S]) here S=ffT N3-cy3, according to standard enzymological analysis. From the Michaelis plot, key values characteristic of a particular enzyme catalyzing a particular reaction can be obtained, namely kpol (defined as the rate constant for the process at infinite substrate concentration) and Kd (defined as the dissociation constant, the concentration of substrate at kpol/2). This process was repeated for clone 9, R713A and R743A mutants.

Figure 8:
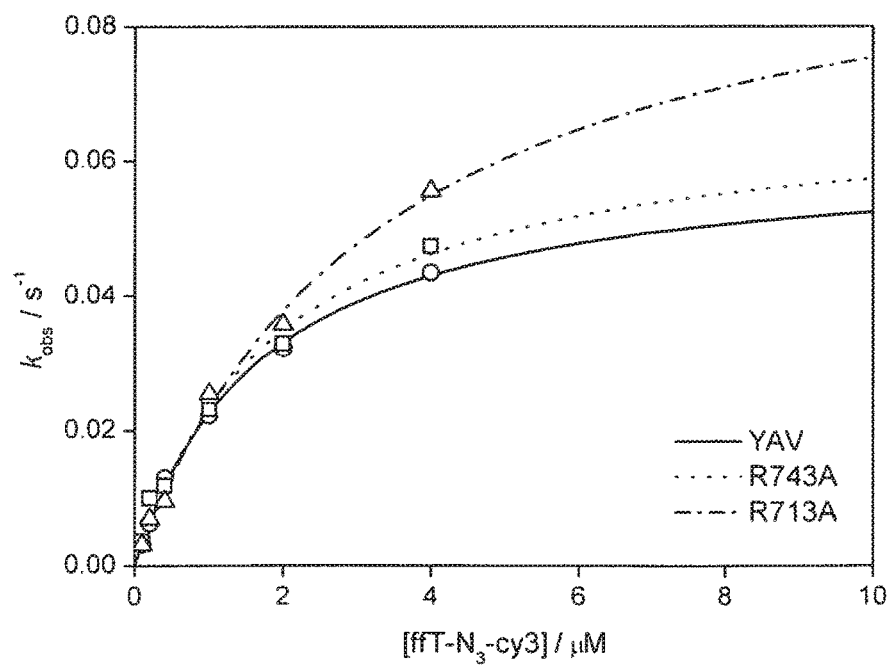
FIG. 8 represents Michaelis plots showing the kinetic characterization of the polymerase enzymes, which are shown overlaid.

Michaelis plots for all of the enzymes are shown overlaid in FIG. 8.

Results

The kinetic characteristics of ffT-N3-cy3 incorporation for the enzymes tested are summarized below.

|  | Clone 9 | R713A | R743A |
|---|---|---|---|
| $k_{pol}/s^{-1}$ | 0.061 | 0.10 | 0.068 |
| $K_d/\mu M$ | 1.72 | 3.32 | 1.92 |

From this, it appears as though the mutations to the DNA-binding region of the polymerases have not adversely affected either the activity of the enzymes (at high substrate concentrations, kpol approximates to Vmax) or the affinity the enzymes have for fully functional nucleotide (in this case ffT-N3-cy3, but the trend is considered to be applicable to all bases). This is an ideal situation, as the mutations have had the desired effect of modifying the DNA-binding affinity of the enzymes without affecting other key catalytic properties.

Example 7—Purification of the Polymerases and Measurement of Levels of Carry Over DNA DNA Contamination Pico green assay (Molecular Probes kit, cat #P11496).

Solutions Required

TE buffer: 10 mM Tris.HCl pH 7.5, 1 mM EDTA 40 mL required, 2 mL of 20×TE buffer added to 38 mL H$_2$O

λ DNA

Solution 1 (2 µg/mL λDNA) dilute 15 µL of λ DNA with 735 λL of 1×TE buffer.

Solution 2 (50 ng/mL λ) dilute 25 µL of A DNA with 975 µl of 1×TE buffer.

Standard Curve

In 2 mL eppendorfs the following samples were made:

| Sample λ DNA (ng) | λ DNA @ 2 mg mL (µL) | λ DNA @ 50 ng mL (µL) | glycerol storage buffer (µL) | TE (µL) |
|---|---|---|---|---|
| 100 | 160 |  | 400 | 1040 |
| 25 | 40 |  | 400 | 1160 |
| 10 | 16 |  | 400 | 1184 |
| 2.5 |  | 160 | 400 | 1040 |
| 1 |  | 64 | 400 | 1136 |
| 0.25 |  | 16 | 400 | 1184 |
| 0.025 |  | 1.6 | 400 | 1198.4 |
| 0 |  |  | 400 | 1200 |

3×500 µL from each sample was put into 3 eppendorfs.

Enzyme Samples

In 5 mL bijou bottles the following samples were made:

| sample |  | Amount (µL) | glycerol storage buffer (µL) | TE (µL) |
|---|---|---|---|---|
| 1 | enzyme stock | 400 |  | 1800 |
| 2 | sample 1 | 1100 | 200 | 900 |
| 3 | sample 2 | 1100 | 200 | 900 |
| 4 | sample 3 | 1100 | 200 | 900 |

2×500 µL from each sample was put into 2 eppendorfs.

A picogreen solution was prepared; 85 µL of picogreen stock added to 17 mL of 1×TE buffer.

500 µL of this solution was added to each of the standard curve and enzyme samples, and was mixed well by pipetting and then all samples were transferred to 1.5 mL fluorimeter cuvettes.

Using the Fluorimeter

The advanced reads program of the Cary Eclipse file was utilised. The λ excitation was set to 480 nm and the λ emission was set to 520 nm, and 1000 volts were used.

Analysis

Data for the standard curve was entered into Graph pad Prism a standard curve of the formula y=ax+c was fitted. The concentration values, x, was then determined.

Results

| Polymerase sample | Concentration of DNA associated with purified polymerase |
|---|---|
| Clone 9 batch 5 | 62.9 ng ± 1.9 ng |
| Clone 9 batch 6 | 63.7 ng ± 2.1 ng |
| Clone 9 R743A | 0.04 ng ± 6.4 ng |
| Clone 9 R713A | 8.2 ng ± 4.2 ng |

From this experiment, it is clear that the alterations in the polymerases enhance purification of the enzyme since less endogenous DNA is carried over during purification. As mentioned above, carry over of endogenous DNA can adversely influence activity of the enzyme and so the mutations are clearly advantageous.

Example 8: Preparation of a Modified Optimised Codon Usage Nucleic Acid Sequence which Encodes the Clone 9 Polymerase The amino acid sequence shown in SEQ ID NO 1 was translated into a nucleic acid sequence using the optimal nucleic acid sequence at each codon to encode for the required/desired amino-acid.

The deduced nucleic acid sequence is shown in SEQ ID NO.19.

In a similar scenario, the nucleic acid sequence presented as SEQ ID NO:20 was deduced based upon the amino-acid sequence of the polymerase presented as SEQ ID NO: 21. The polymerase having the amino acid sequence presented as SEQ ID NO: 21 comprises the R743A mutation and also carries a substitution mutation to Serine at both residues 141 and 143. Nucleic acid molecules and proteins comprising the respective nucleotide and amino acid sequences form a part of the invention.

Cloning of a Codon-Modified Gene of Clone 9 into the Expression Vector pET11-a Using NdeI-Nhe I Sites (to Preserve the Internal Bam H I Site).
Synthesis of a Codon-Optimised Gene of Clone 9

The nucleic acid sequence of SEQ ID NO 19 was synthesized and supplied in pPCR-Script by GENEART.

The DNA and protein sequences were confirmed (results not shown).

Cloning of pSV57 (Codon-Modified Gene of Clone 9 in the pPCRScript Vector) into pET11-a (Hereinafter Named pSV 52)
Preparation of the pET11-a Vector The pET11-a vector (Novagen catalog No. 69436-3) was digested with Nde I and Nhe I, dephosphorylated, and any undigested vector ligated using standard techniques.

The digested vector was purified on a 0.8% agarose gel and using the MinElute® Gel extraction kit protocol from Qiagene.

The purified digested pET11-a vector was quantified using a polyacrylamide TB 4-20% gel.
Preparation of the Insert (Codon-Modified Gene of Clone 9)

The codon-modified gene of clone 9 synthesized by GENEART in the pPCRSCript vector (hereinafter pSV 57) was digested with Nde I and Nhe.

The digested insert was purified on a 0.8% agarose gel and using the MinElute® Gel extraction kit protocol from Qiagen®.

The purified digested insert was quantified using a polyacrylamide TB 4-20% gel.
Ligation The pET11-a vector and the insert were ligated (ratio 1:3) at the Nde I and Nhe I restriction sites using the Quick ligation kit (NEB. M2200S).
Transformation 2 µl of the ligation mixture was used to transform XL10-gold ultracompetent cells (Stratagene catalog No 200315). PCR screening of the colonies containing the insert.

Transformants were picked and DNA minipreps of 3 positive clones of XL10-gold transformed with the ligation product were prepared. The three purified plasmids (hereinafter pSV52, clones 1, 2 and 4 were sequenced at the cloning sites and all three clones were found to have the correct sequence at the cloning sites.

The minipreps were also used to transform the expression E. coli host BL21-CodonPlus (DE3)-RIL (Stratagene catalog No. 230245) as described below.
Southern Blotting pVent (pNEB917 derived vector), pSV43 (clone 9 in pET11a), pSV54 (codon-optimised clone in pET11-a) and pSV57 (codon-modified gene in pPCR-Script supplied by GENEART) were restricted and Southern blotted to check for cross hybridisation between the genes (results not shown).

Expression Studies of Pol 52

Transformation of pSV52 (clones 1, 2 and 4) into the expression host E. coli BL21-CodonPlus (DE3) RIL (Stratagene catalog No 230245).

21-25 ng of purified pSV52 plasmid DNA (clones 1, 2 and 4) was used to transform competent cells of the expression host E. coli BL21-CodonPlus (DB3) RIL (hereinafter RIL) using the manufacturer's instructions.

50 µl of each transformation was plated onto fresh Luria-Bertani (LB) agar medium containing 100 µg/ml of carbenicillin and 34 µg/ml of chloramphenicol (LBCC agar medium) and incubated overnight at 37° C.

The following glycerol stocks were also plated onto LBCC agar plates to be used as controls for the expression studies and incubated overnight at 37° C.
SOL10204:RIL-pSV19 (clone 9 in pNEB 917 vector)
SOL10354:RIL-pSV43 (clone 9 in pET11-a vector)
Production of Cell Pellets Expressing Pol 52 and the Positive Controls of Clone 9

Single transformed E. coli colonies were used to inoculate starter cultures of 3 ml LBCC media in culture tubes and incubated overnight at 37° C. with shaking (225 rpm).

The starter cultures were diluted 1/100 into 50 ml LBCC media in sterile vented Erlenmeyer flasks and incubated at 37° C. with vigorous shaking (300 rpm) for approximately 4 hours until $OD_{600nm}$ was approximately 1.0.

10 ml of the uninduced cultures was removed and the cells harvested (as described below).

IPTG was added to a final concentration of 1 mM and the cultures induced for 2 hours at 37° C. with vigorous shaking (300 rpm).

10 ml of the induced cultures was removed and the cells harvested as follows:

Induced and uninduced cells were harvested by centrifugation at 5000×g for 30 min at 4° C.

The cell pellets were washed and resuspended in $\frac{1}{10}^{th}$ of the culture volume of 1× Phosphate Buffered Saline (PBS) and centrifuged as above.

The supernatants were decanted and the pellets stored at −20° C. until required for the cell lysis and purification steps.
Cell Lysis and Crude Purification of Pol 52 and Clone 9

The cell pellets were thawed and resuspended in $\frac{1}{50}^{th}$ of culture volume of 1× Wash buffer (50 mM Tris-HCl pH 7.9, 50 mM glucose, 1 mM EDTA) containing 4 mg/ml lysozyme freshly added to the 1× buffer and incubated at room temperature for 15 min.

An equal volume of 1× Lysis buffer (10 mM Tris-HCl pH 7.9, 50 mM KCl, 1 mM EDTA, 0.5% (w/v) Tween 20) containing 0.5% (w/v) Tergitol NP-40 and 1× "complete EDTA-free" proteinase inhibitor cocktail (both added freshly to the 1× Lysis buffer) was added to the cells which were gently mixed and incubated at room temperature for 30 min.

The cells were heated at 80° C. for 1 hr in a water bath then centrifuged at 38,800×g for 30 min at 4° C. to remove cell debris and denatured protein.
Preparation of Samples Normalised for Volume and SDS-PAGE Analysis The expression of Pol 52 and clone 9 DNA polymerases was assessed by analysis of the crude lysates of the uninduced and induced control samples on SDS-PAGE followed by Coomassie blue staining.

Supernatants were carefully removed and the samples normalised to volume by the addition of 50:50 (v/v) 1× Wash buffer and 1× Lysis buffer to a final volume of 370 µl.

Preparation of Samples for Gel I

10 µl of the normalised crude lysates (from uninduced and induced samples) were mixed with 10 µl of loading buffer containing 143 mM DTT.

Preparation of Samples for Gel II

Normalised crude lysates from the induced samples only were dilute ⅟10 in distilled water to a final volume of 10 µl and mixed with 10 µl of loading buffer containing 143 mM DTT.

All samples were heated at 70° C. for 10 minutes.

SDS-PAGE

A NUPage® 4-12% Bis-Tris gel (Invitrogen catalog No NP0321BOX) was prepared according to the manufacturer's instructions.

10 µl of SeeBlue® Plus2 pre-stained proteins standard (Invitrogen catalog No LC5925) and µl of each sample were loaded and the gels run at a constant 200V for 50 minutes.

The gels were stained with Coomassie blue (SimplyBlue Safe stain, Invitrogen, catalog No. LC 6060).

Results

Figure 10:
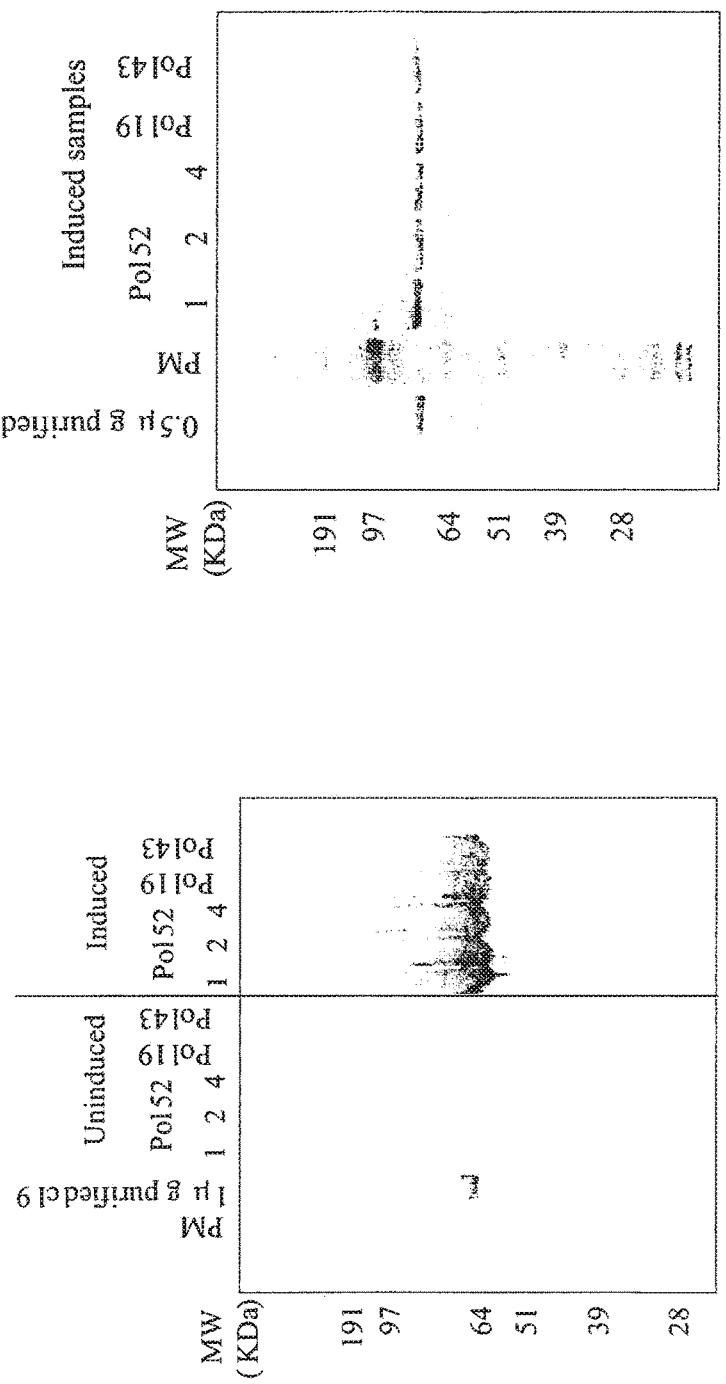
FIG. 10 presents the results of SDS-PAGE experiments comparing the expression of 3 clones (1, 2 and 4) of Pol 52 (codon-modified gene of clone 9 when expressed in pET11-a expression vector) with Pol 19 (clone 9 gene expressed from the pNEB917 expression vector) and Pol 43 (clone 9 gene expressed from the pET11-a expression vector) in the crude lysates of uninduced (gel I) and induced (Gel 1.11) cultures.

The results of the SDS-PAGE are shown in FIG. 10.

The estimated expression level in this experiment is 20 mg/L of culture.

Similar levels of expression of the codon-modified gene of clone 9 in *E. coli* host BL21-CodonPlus (DE3)-RIL (Pol52) were obtained using the expression vector pET11-a when compared to the un-modified gene of clone 9 in the same cells using either the expression vector pNEB917 (Pol19) or pET11 (Pol 43).

No significant differences were observed in the levels of expression of the 3 different clones of Pol 52.

REFERENCES

Crystal structure of a bacteriophage T7 DNA replication complex at 2.2 Å resolution.
Doublie et al. 1998. Nature 391, 251.
Function of the C-terminus of Phi29 DNA polymerase in DNA and terminal protein binding.
Truniger et al. 2004. Nucleic Acids Research 32, 371.
A thumb subdomain mutant of the large fragment of *Escherichia coli* DNA polymerase I with reduced DNA binding affinity, processivity and frameshift fidelity.
Minnick et al. 1996. J. Biol. Chem., 271. 24954.
Identification of residues critical for the polymerase activity of the Klenow fragment of DNA polymerase I from *Escherichia coli*.
Polesky et al. 1990. J. Biol. Chem., 265, 14579.
Cloning of thermostable DNA polymerases from hyperthermophilic marine archaea with emphasis on *Thermococcus* sp. 9°N-7 and mutations affecting 3'-5' exonuclease activity.
Southworth et al. 1996. PNAS. 93, 5281
Structure of the replicating complex of a pol alpha family DNA polymerase. Franklin et al. 2001. Cell 105, 657.
Crystal structure of a pol alpha family DNA polymerase from the hyperthermophilic archaeon *Thermococcus* sp. 9°N-7.
Rodriguez et al. 2000. J. Mol. Biol., 299, 471.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

The invention claimed is:

1. An altered family B polymerase having a reduced affinity for DNA, wherein the polymerase comprises at least two substitution mutations selected from the positions functionally equivalent to Lys705, Arg713, and Arg743 of the 9° N DNA polymerase amino acid sequence of SEQ ID NO:22.

2. The altered polymerase of claim 1, wherein the polymerase comprises substitution mutations at the positions functionally equivalent to Lys705, Arg713, and Arg743 of the 9° N DNA polymerase amino acid sequence of SEQ ID NO:22.

3. The altered polymerase of claim 2, wherein each substitution mutation is to a non-polar amino acid.

4. The altered polymerase of claim 3, wherein the non-polar amino acid is alanine, glycine, or methionine.

5. The altered polymerase of claim 1, wherein the polymerase further comprises a substitution mutation at the position functionally equivalent to Arg606, His679, or the combination thereof, of the 9° N DNA polymerase amino acid sequence of SEQ ID NO:22.

6. The altered polymerase of claim 1, wherein the polymerase further comprises a substitution mutation at the position functionally equivalent to Leu408, Tyr409, Pro410, or a combination thereof, of the 9° N DNA polymerase amino acid sequence of SEQ ID NO:22.

7. The altered polymerase of claim 1, wherein the polymerase is a family B archaeal polymerase.

8. A kit for performing a nucleotide incorporation reaction, said kit comprising: a polymerase as defined in claim 1 and a nucleotide solution.

9. The kit of claim 8, wherein the nucleotide solution comprises labelled nucleotides.

10. The kit of claim 8, wherein the nucleotides comprise synthetic nucleotides.

11. The kit of claim 8, wherein the nucleotides comprise modified nucleotides.

12. The kit of claim 11, wherein the modified nucleotides have been modified at the 3' sugar hydroxyl such that the substituent is larger in size than the naturally occurring 3' hydroxyl group.

13. The kit of claim 11, wherein modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", C(R')$_2$—S—R", and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy, or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, which intermediate dissociates under aqueous conditions to afford a molecule with a free 3'OH;

with the proviso that where Z is —C(R')$_2$—S—R", both R' groups are not H.

14. The kit of claim 13, wherein R' of the modified nucleotide or nucleoside is an alkyl or substituted alkyl.

15. The kit of claim 14, wherein Z is of formula —C(R')$_2$—N$_3$.

16. The kit of claim 14, wherein Z is an azidomethyl group.

17. The kit of claim 11, wherein the modified nucleotides are fluorescently labelled to allow their detection.

18. The kit of claim 11, wherein the modified nucleotides comprise a nucleotide or nucleoside having a base attached to a detectable label via a cleavable linker, wherein the cleavable linker contains a moiety selected from the group consisting of:

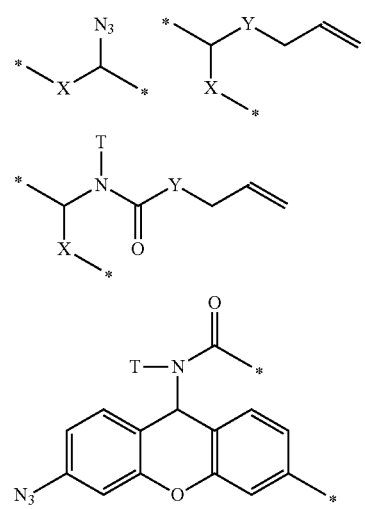

wherein X is selected from the group consisting of O, S, NH and NQ wherein Q is a C$_{1-10}$ substituted or unsubstituted alkyl group, Y is selected from the group comprising O, S, NH and N(allyl), T is hydrogen or a C$_{1-10}$ substituted or unsubstituted alkyl group and * indicates where the moiety is connected to the remainder of the nucleotide or nucleoside.

19. The kit of claim 18, wherein the detectable label comprises a fluorescent label.

20. The kit of claim 8, further comprising one or more DNA template molecules, primers, or a combination thereof.

* * * * *

SEQUENCE LISTING

<160> NUMBER OF SEQ ID NOS: 24

<210> SEQ ID NO 1
<211> LENGTH: 775
<212> TYPE: PRT
<213> ORGANISM: Artificial sequence
<220> FEATURE:
<223> OTHER INFORMATION: Mutant polymerase

<400> SEQUENCE: 1

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
```

```
                130                 135                 140
Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Val Ser Ile Ile Thr His
            405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560
```

```
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
690                 695                 700
Ala Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
            740                 745                 750
Glu Asp Leu Arg Tyr Gln Lys Thr Lys Gln Val Gly Leu Gly Ala Trp
        755                 760                 765
Leu Lys Val Lys Gly Lys Lys
    770                 775

<210> SEQ ID NO 2
<211> LENGTH: 2328
<212> TYPE: DNA
<213> ORGANISM: Artificial sequence
<220> FEATURE:
<223> OTHER INFORMATION: Mutant polymerase

<400> SEQUENCE: 2
atgattctcg ataccgacta catcaccgag aacgggaagc ccgtgataag ggtcttcaag      60
aaggagaacg gcgagtttaa aatcgagtac gacagaacct tcgagcccta cttctacgcc     120
cttctgaagg acgattctgc gatagaggac gtcaagaagg taaccgcaaa gaggcacgga     180
acggttgtca aggtgaagcg cgccgagaag gtgcagaaga gttcctcgg caggccgata     240 gaggtctgga agctctactt caaccatcct caggacgtcc cggcgattcg agacaggata     300
cgtgcccacc ccgctgtcgt tgacatctac gagtacgaca tacccttcgc caagcgctac     360
ctcatcgaca agggcctgat tccgatggag ggcgacgagg agcttacgat gctcgccttc     420
gcgatcgcaa ccctctatca cgagggcgag gagttcggaa ccgggccgat tctcatgata     480
agctacgccg acgggagcga ggcgagggtg ataacctgga agaagattga ccttccgtac     540
gttgacgtcg tctcgaccga gaaggagatg attaagcgct tcctccgcgt cgtcagggag     600
aaggaccccg acgtgctcat cacctacaac ggcgacaact tcgacttcgc ctacctgaag     660
aagcgctctg aggaactcgg aataaagttc acactcggca gggacgggag cgagccgaag     720
atacagcgaa tgggcgaccg cttttgccgtt gaggtgaagg gcaggattca cttcgacctc     780
```

| | |
|---|---|
| taccccgtca taaggcgcac gataaacctc ccgacctaca cccttgaggc cgtttacgag | 840 |
| gccgtctttg aaagcccaa ggagaaggtt tacgcagagg agatagcgca ggcctgggag | 900 |
| agcggggagg gccttgaaag ggttgcaaga tactcgatgg aggacgctaa ggtgacctac | 960 |
| gagctgggaa gggagttctt cccgatggag gcccagcttt cgaggcttat aggccagagc | 1020 |
| ctctgggacg tctcgcgctc gagcaccgga aatttggtgg agtggttcct cctgcggaag | 1080 |
| gcctacaaga ggaacgagct cgccccaaac aagcccgacg agaggagct cgcgagacgg | 1140 |
| cgcggggggct acgctggcgg gtacgttaag gaaccagagc ggggattgtg ggacaacatt | 1200 |
| gtgtatctag acttccgctc gtatgcggtt tcaatcatca taaccacaa cgtctcgccg | 1260 |
| gataccctca accgcgaggg ctgtaaagag tacgacgtcg cccctgaggt tggacacaag | 1320 |
| ttctgcaagg acttccccgg cttcatacca agcctcctgg gagatttgct cgaggagagg | 1380 |
| cagaagataa agcggaagat gaaggcaacg gttgacccgc tggagaagaa actcctcgat | 1440 |
| tacaggcaga ggctgatcaa aatcctcgcc aacagcttct acggctacta cggctacgcc | 1500 |
| aaggcccggt ggtactgcaa ggagtgcgcc gagagcgtta cggcctgggg aagggagtat | 1560 |
| atagaaatgg ttatccggga actcgaagaa aaattcggtt ttaaagttct ctatgccgat | 1620 |
| acagacggtc tccatgctac cattcccgga gcagacgctg aaacagtcaa gaaaaaagca | 1680 |
| aaggagttct taaatacat taatccaaaa ctgcccggcc tgctcgaact tgagtacgag | 1740 |
| ggcttctacg tgagggggctt cttcgtcacg aagaagaagt acgctgtgat agacgaggag | 1800 |
| ggcaagataa ccacgagggg tcttgagatt gtgaggcgcg actggagcga gatagcgaag | 1860 |
| gagacccagg ccagggtctt agaggcgata ctcaagcacg gtgacgtcga ggaggccgtt | 1920 |
| aggatagtca aggaagtgac ggaaaagctg agcaagtatg aggtcccgcc cgagaagctg | 1980 |
| gtaatccacg agcagataac cgcgatttg agggattaca aagccaccgg cccgcacgtt | 2040 |
| gccgttgcga agaggctcgc ggcgcgtgga gtgaaaatcc ggcccggcac ggtgataagc | 2100 |
| tacatcgtcc tagcgggctc tggaaggata ggcgacaggg cgattccagc tgatgagttc | 2160 |
| gaccccgacga agcaccgcta cgatgcggaa tactacatcg agaaccaggt tctcccggcg | 2220 |
| gtggagagga ttctaaaagc cttcggctat cggaaggagg atttgcgcta ccagaagacg | 2280 |
| aagcaggtcg gcttgggcgc gtggctgaag gtgaagggga agaagtga | 2328 |

<210> SEQ ID NO 3
<211> LENGTH: 775
<212> TYPE: PRT
<213> ORGANISM: Artificial sequence
<220> FEATURE:
<223> OTHER INFORMATION: Mutant polymerase

<400> SEQUENCE: 3

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

```
Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Val Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510
```

```
Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
    690                 695                 700

Lys Gly Ser Gly Arg Ile Gly Asp Ala Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
    755                 760                 765

Leu Lys Val Lys Gly Lys Lys
    770                 775

<210> SEQ ID NO 4
<211> LENGTH: 2328
<212> TYPE: DNA
<213> ORGANISM: Artificial sequence
<220> FEATURE:
<223> OTHER INFORMATION: Mutant polymerase

<400> SEQUENCE: 4
atgattctcg ataccgacta catcaccgag aacgggaagc ccgtgataag ggtcttcaag      60
aaggagaacg gcgagtttaa aatcgagtac gacagaacct tcgagcccta cttctacgcc     120
cttctgaagg acgattctgc gatagaggac gtcaagaagg taaccgcaaa gaggcacgga     180
acggttgtca aggtgaagcg cgccgagaag gtgcagaaga agttcctcgg caggccgata     240
gaggtctgga agctctactt caaccatcct caggacgtcc cggcgattcg agacaggata     300
cgtgcccacc ccgctgtcgt tgacatctac gagtacgaca taccctttgc caagcgctac     360
ctcatcgaca agggcctgat tccgatggag ggcgacgagg agcttacgat gctcgccttc     420
gcgatcgcaa ccctctatca cgagggcgag gagttcggaa ccgggccgat tctcatgata     480
agctacgccg acgggagcga ggcgagggtg ataacctgga agaagattga ccttccgtac     540
```

```
gttgacgtcg tctcgaccga aaggagatg attaagcgct tcctccgcgt cgtcagggag      600
aaggaccccg acgtgctcat cacctacaac ggcgacaact tcgacttcgc ctacctgaag     660
aagcgctctg aggaactcgg aataaagttc acactcggca gggacgggag cgagccgaag     720
atacagcgaa tgggcgaccg cttttgccgtt gaggtgaagg gcaggattca cttcgacctc     780
taccccgtca taaggcgcac gataaacctc ccgacctaca cccttgaggc cgtttacgag      840
gccgtctttg aaagcccaa ggagaaggtt tacgcagagg agatagcgca ggcctgggag      900
agcggggagg gccttgaaag ggttgcaaga tactcgatgg aggacgctaa ggtgacctac      960
gagctgggaa gggagttctt cccgatggag gcccagcttt cgaggcttat aggccagagc     1020
ctctgggacg tctcgcgctc gagcaccgga aatttggtgg agtggttcct cctgcggaag     1080
gcctacaaga ggaacgagct cgccccaaac aagcccgacg agagggagct cgcgagacgg     1140
cgcgggggct acgctggcgg gtacgttaag gaaccagagc ggggattgtg ggacaacatt     1200
gtgtatctag acttccgctc gtatgcggtt tcaatcatca tacccacaa cgtctcgccg      1260 gataccctca accgcgaggg ctgtaaagag tacgacgtcg cccctgaggt tggacacaag     1320
ttctgcaagg acttccccgg cttcatacca agcctcctgg agatttgct cgaggagagg     1380 cagaagataa agcggaagat gaaggcaacg gttgacccgc tggagaagaa actcctcgat     1440
tacaggcaga ggctgatcaa aatcctcgcc aacagcttct acggctacta cggctacgcc     1500
aaggcccggt ggtactgcaa ggagtgcgcc gagagcgtta cggcctgggg aagggagtat     1560
atagaaatgg ttatccggga actcgaagaa aaattcggtt ttaaagttct ctatgccgat     1620
acagacggtc tccatgctac cattcccgga gcagacgctg aaacagtcaa gaaaaaagca     1680
aaggagttct taaaatacat taatccaaaa ctgcccggcc tgctcgaact tgagtacgag     1740
ggcttctacg tgaggggctt cttcgtcacg aagaagaagt acgctgtgat agacgaggag     1800
ggcaagataa ccacgagggg tcttgagatt gtgaggcgcg actggagcga gatagcgaag     1860
gagacccagg ccagggtctt agaggcgata ctcaagcacg gtgacgtcga ggaggccgtt     1920
aggatagtca aggaagtgac ggaaaagctg agcaagtatg aggtcccgcc gagaagctg     1980 gtaatccacg agcagataac gcgcgatttg agggattaca aagccaccgg cccgcacgtt     2040
gccgttgcga agaggctcgc ggcgcgtgga gtgaaaatcc ggcccggcac ggtgataagc     2100
tacatcgtcc taagggctc tggaaggata ggcgacgcgg cgattccagc tgatgagttc     2160 gaccccgacga agcaccgcta cgatgcggaa tactacatcg agaaccaggt tctcccggcg     2220
gtggagagga ttctaaaagc cttcggctat cggaaggagg atttgcgcta ccagaagacg     2280
aagcaggtcg gcttgggcgc gtggctgaag gtgaagggga agaagtga                  2328
```

<210> SEQ ID NO 5
<211> LENGTH: 775
<212> TYPE: PRT
<213> ORGANISM: Artificial sequence
<220> FEATURE:
<223> OTHER INFORMATION: Mutant polymerase

<400> SEQUENCE: 5

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45
```

-continued

Glu Asp Val Lys Lys Val Thr Ala Lys Arg His Gly Thr Val Val Lys
 50              55                  60

Val Lys Arg Ala Glu Lys Val Gln Lys Lys Phe Leu Gly Arg Pro Ile
65              70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
                180                 185                 190

Arg Phe Leu Arg Val Val Arg Glu Lys Asp Pro Asp Val Leu Ile Thr
    195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Val Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp

Tyr Arg Gln Arg Leu Ile Lys Ile Leu Ala Asn Ser Phe Tyr Gly Tyr
465                 470                 475                 480

Tyr Gly Tyr Ala Lys Ala Arg Trp Tyr Cys Lys Glu Cys Ala Glu Ser
        485                 490                 495

Val Thr Ala Trp Gly Arg Glu Tyr Ile Glu Met Val Ile Arg Glu Leu
    500                 505                 510

Glu Glu Lys Phe Gly Phe Lys Val Leu Tyr Ala Asp Thr Asp Gly Leu
515                 520                 525

His Ala Thr Ile Pro Gly Ala Asp Ala Glu Thr Val Lys Lys Lys Ala
530                 535                 540

Lys Glu Phe Leu Lys Tyr Ile Asn Pro Lys Leu Pro Gly Leu Leu Glu
545                 550                 555                 560

Leu Glu Tyr Glu Gly Phe Tyr Val Arg Gly Phe Phe Val Thr Lys Lys
        565                 570                 575

Lys Tyr Ala Val Ile Asp Glu Glu Gly Lys Ile Thr Thr Arg Gly Leu
    580                 585                 590

Glu Ile Val Arg Arg Asp Trp Ser Glu Ile Ala Lys Glu Thr Gln Ala
595                 600                 605

Arg Val Leu Glu Ala Ile Leu Lys His Gly Asp Val Glu Glu Ala Val
610                 615                 620

Arg Ile Val Lys Glu Val Thr Glu Lys Leu Ser Lys Tyr Glu Val Pro
625                 630                 635                 640

Pro Glu Lys Leu Val Ile His Glu Gln Ile Thr Arg Asp Leu Arg Asp
        645                 650                 655

Tyr Lys Ala Thr Gly Pro His Val Ala Val Ala Lys Arg Leu Ala Ala
    660                 665                 670

Arg Gly Val Lys Ile Arg Pro Gly Thr Val Ile Ser Tyr Ile Val Leu
675                 680                 685

Lys Gly Ser Gly Arg Ile Gly Asp Arg Ala Ile Pro Ala Asp Glu Phe
690                 695                 700

Asp Pro Thr Lys His Arg Tyr Asp Ala Glu Tyr Tyr Ile Glu Asn Gln
705                 710                 715                 720

Val Leu Pro Ala Val Glu Ala Ile Leu Lys Ala Phe Gly Tyr Arg Lys
        725                 730                 735

Glu Asp Leu Arg Tyr Gln Lys Thr Lys Gln Val Gly Leu Gly Ala Trp
    740                 745                 750

Leu Lys Val Lys Gly Lys Lys
755                 760                 765

770                 775

<210> SEQ ID NO 6
<211> LENGTH: 2328
<212> TYPE: DNA
<213> ORGANISM: Artificial sequence
<220> FEATURE:
<223> OTHER INFORMATION: Mutant polymerase

<400> SEQUENCE: 6
atgattctcg ataccgacta catcaccgag aacgggaagc ccgtgataag ggtcttcaag    60
aaggagaacg gcgagtttaa aatcgagtac gacagaacct tcgagcccta cttctacgcc   120
cttctgaagg acgattctgc gatagaggac gtcaagaagg taaccgcaaa gaggcacgga   180
acggttgtca aggtgaagcg cgccgagaag gtgcagaaga agttcctcgg caggccgata   240
gaggtctgga agctctactt caaccatcct caggacgtcc cggcgattcg agacaggata   300

| | |
|---|---|
| cgtgcccacc cgctgtcgt tgacatctac gagtacgaca tacccttcgc caagcgctac | 360 |
| ctcatcgaca agggcctgat tccgatggag ggcgacgagg agcttacgat gctcgccttc | 420 |
| gcgatcgcaa ccctctatca cgagggcgag gagttcggaa ccgggccgat tctcatgata | 480 |
| agctacgccg acgggagcga ggcgagggtg ataacctgga agaagattga ccttccgtac | 540 |
| gttgacgtcg tctcgaccga aggagagatg attaagcgct tcctccgcgt cgtcagggag | 600 |
| aaggaccccg acgtgctcat cacctacaac ggcgacaact tcgacttcgc ctacctgaag | 660 |
| aagcgctctg aggaactcgg aataaagttc acactcggca gggacgggag cgagccgaag | 720 |
| atacagcgaa tgggcgaccg ctttgccgtt gaggtgaagg caggattca cttcgacctc | 780 |
| taccccgtca taaggcgcac gataaacctc ccgacctaca cccttgaggc cgtttacgag | 840 |
| gccgtctttg aaagcccaa ggagaaggtt tacgcagagg agatagcgca ggcctgggag | 900 |
| agcggggagg gccttgaaag ggttgcaaga tactcgatgg aggacgctaa ggtgacctac | 960 |
| gagctgggaa gggagttctt cccgatggag gcccagcttt cgaggcttat aggccagagc | 1020 |
| ctctgggacg tctcgcgctc gagcaccgga aatttggtgg agtggttcct cctgcggaag | 1080 |
| gcctacaaga ggaacgagct cgccccaaac aagcccgacg agagggagct cgcgagacgg | 1140 |
| cgcgggggct acgctggcgg gtacgttaag gaaccagagc ggggattgtg ggacaacatt | 1200 |
| gtgtatctag acttccgctc gtatgcggtt tcaatcatca tacccacaa cgtctcgccg | 1260 |
| gatacccctca accgcgaggg ctgtaaagag tacgacgtcg cccctgaggt tggacacaag | 1320 |
| ttctgcaagg acttccccgg cttcatacca agcctcctgg agatttgct cgaggagagg | 1380 |
| cagaagataa agcggaagat gaaggcaacg gttgacccgc tggagaagaa actcctcgat | 1440 |
| tacaggcaga ggctgatcaa atcctcgcc aacagcttct acggctacta cggctacgcc | 1500 |
| aaggcccggt ggtactgcaa ggagtgcgcc gagagcgtta cggcctgggg aagggagtat | 1560 |
| atagaaatgg ttatccggga actcgaagaa aaattcggtt ttaaagttct ctatgccgat | 1620 |
| acagacggtc tccatgctac cattcccgga gcagacgctg aaacagtcaa gaaaaaagca | 1680 |
| aaggagttct taaatacat taatccaaaa ctgcccggcc tgctcgaact tgagtacgag | 1740 |
| ggcttctacg tgagggggctt cttcgtcacg aagaagaagt acgctgtgat agacgaggag | 1800 |
| ggcaagataa ccacgagggg tcttgagatt gtgaggcgcg actggagcga gatagcgaag | 1860 |
| gagacccagg ccagggtctt agaggcgata ctcaagcacg gtgacgtcga ggaggccgtt | 1920 |
| aggatagtca aggaagtgac ggaaaagctg agcaagtatg aggtcccgcc cgagaagctg | 1980 |
| gtaatccacg agcagataac gcgcgatttg agggattaca aagccaccgg cccgcacgtt | 2040 |
| gccgttgcga agaggctcgc ggcgcgtgga gtgaaaatcc ggcccggcac ggtgataagc | 2100 |
| tacatcgtcc taaagggctc tggaaggata ggcgacaggg cgattccagc tgatgagttc | 2160 |
| gacccgacga agcaccgcta cgatgcggaa tactacatcg agaaccaggt tctcccggcg | 2220 |
| gtggaggcga ttctaaaagc cttcggctat cggaaggagg atttgcgcta ccagaagacg | 2280 |
| aagcaggtcg gcttgggcgc gtggctgaag gtgaagggga agaagtga | 2328 |

<210> SEQ ID NO 7
<211> LENGTH: 704
<212> TYPE: PRT
<213> ORGANISM: Artificial sequence
<220> FEATURE:
<223> OTHER INFORMATION: Mutant polymerase

<400> SEQUENCE: 7

Met Ile Leu Asp Thr Asp Tyr Ile Thr Glu Asn Gly Lys Pro Val Ile

-continued

```
1               5                   10                  15
Arg Val Phe Lys Lys Glu Asn Gly Glu Phe Lys Ile Glu Tyr Asp Arg
                20                  25                  30
Thr Phe Glu Pro Tyr Phe Tyr Ala Leu Leu Lys Asp Asp Ser Ala Ile
                35                  40                  45
Glu Asp Val Lys Lys Val Thr Ala Lys Arg His Gly Thr Val Val Lys
                50                  55                  60
Val Lys Arg Ala Glu Lys Val Gln Lys Lys Phe Leu Gly Arg Pro Ile
65                  70                  75                  80
Glu Val Trp Lys Leu Tyr Phe Asn His Pro Gln Asp Val Pro Ala Ile
                85                  90                  95
Arg Asp Arg Ile Arg Ala His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Thr Met Leu Ala Phe Ala Ile Ala Thr
                130                 135                 140
Leu Tyr His Glu Gly Glu Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
                180                 185                 190
Arg Phe Leu Arg Val Val Arg Glu Lys Asp Pro Asp Val Leu Ile Thr
                195                 200                 205
Tyr Asn Gly Asp Asn Phe Asp Phe Ala Tyr Leu Lys Lys Arg Ser Glu
                210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
                275                 280                 285
Lys Val Tyr Ala Glu Glu Ile Ala Gln Ala Trp Glu Ser Gly Glu Gly
                290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
                370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Tyr Ala Val Ser Ile Ile Thr His
                405                 410                 415
Asn Val Ser Pro Asp Thr Leu Asn Arg Glu Gly Cys Lys Glu Tyr Asp
                420                 425                 430
```

```
Val Ala Pro Glu Val Gly His Lys Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Arg Lys Met Lys Ala Thr Val Asp Pro Leu Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
        515                 520                 525
Glu Glu Lys Phe Gly Phe Lys Val Leu Tyr Ala Asp Thr Asp Gly Leu
    530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
    690                 695                 700
```

<210> SEQ ID NO 8
<211> LENGTH: 2328
<212> TYPE: DNA
<213> ORGANISM: Artificial sequence
<220> FEATURE:
<223> OTHER INFORMATION: Mutant polymerase

<400> SEQUENCE: 8

| | | | | | | |
|---|---|---|---|---|---|---|
| atgattctcg | ataccgacta | catcaccgag | aacgggaagc | ccgtgataag | ggtcttcaag | 60 |
| aaggagaacg | gcgagtttaa | aatcgagtac | gacagaacct | tcgagcccta | cttctacgcc | 120 |
| cttctgaagg | acgattctgc | gatagaggac | gtcaagaagg | taaccgcaaa | gaggcacgga | 180 |
| acggttgtca | aggtgaagcg | cgccgagaag | gtgcagaaga | gttcctcgg | caggccgata | 240 |
| gaggtctgga | agctctactt | caaccatcct | caggacgtcc | cggcgattcg | agacaggata | 300 |
| cgtgcccacc | ccgctgtcgt | tgacatctac | gagtacgaca | tacccttcgc | caagcgctac | 360 |
| ctcatcgaca | agggcctgat | tccgatggag | ggcgacgagg | agcttacgat | gctcgccttc | 420 |
| gcgatcgcaa | ccctctatca | cgagggcgag | gagttcggaa | ccgggccgat | tctcatgata | 480 |
| agctacgccg | acgggagcga | ggcgagggtg | ataacctgga | agaagattga | ccttccgtac | 540 |

```
gttgacgtcg tctcgaccga aaggagatg attaagcgct tcctccgcgt cgtcagggag    600
aaggaccccg acgtgctcat cacctacaac ggcgacaact tcgacttcgc ctacctgaag    660
aagcgctctg aggaactcgg aataaagttc acactcggca gggacgggag cgagccgaag    720
atacagcgaa tgggcgaccg cttttgccgtt gaggtgaagg gcaggattca cttcgacctc    780
taccccgtca taaggcgcac gataaacctc ccgacctaca cccttgaggc cgtttacgag    840
gccgtctttg gaaagcccaa ggagaaggtt tacgcagagg agatagcgca ggcctgggag    900
agcggggagg gccttgaaag ggttgcaaga tactcgatgg aggacgctaa ggtgacctac    960
gagctgggaa gggagttctt cccgatggag gcccagcttt cgaggcttat aggccagagc   1020
ctctgggacg tctcgcgctc gagcaccgga aatttggtgg agtggttcct cctgcggaag   1080
gcctacaaga ggaacgagct cgccccaaac aagcccgacg agagggagct cgcgagacgg   1140 cgcggggct acgctggcgg gtacgttaag gaaccagagc ggggattgtg ggacaacatt   1200
gtgtatctag acttccgctc gtatgcggtt tcaatcatca taaccacaa cgtctcgccg   1260 gataccctca accgcgaggg ctgtaaagag tacgacgtcg cccctgaggt tggacacaag   1320
ttctgcaagg acttccccgg cttcatacca agcctcctgg gagatttgct cgaggagagg   1380
cagaagataa agcggaagat gaaggcaacg gttgacccgc tggagaagaa actcctcgat   1440
tacaggcaga ggctgatcaa aatcctcgcc aacagcttct acggctacta cggctacgcc   1500
aaggcccggt ggtactgcaa ggagtgcgcc gagagcgtta cggcctgggg aagggagtat   1560
atagaaatgg ttatccggga actcgaagaa aaattcggtt ttaaagttct ctatgccgat   1620
acagacggtc tccatgctac cattcccgga gcagacgctg aaacagtcaa gaaaaaagca   1680
aaggagttct taaatacat taatccaaaa ctgcccggcc tgctcgaact tgagtacgag   1740
ggcttctacg tgaggggctt cttcgtcacg aagaagaagt acgctgtgat agacgaggag   1800
ggcaagataa ccacgagggg tcttgagatt gtgaggcgcg actggagcga gatagcgaag   1860
gagacccagg ccagggtctt agaggcgata ctcaagcacg gtgacgtcga ggaggccgtt   1920
aggatagtca aggaagtgac ggaaaagctg agcaagtatg aggtcccgcc cgagaagctg   1980
gtaatccacg agcagataac gcgcgatttg agggattaca aagccaccgg cccgcacgtt   2040
gccgttgcga agaggctcgc ggcgcgtgga gtgaaaatcc ggcccggcac ggtgataagc   2100
tacatcgtcc tgacgggctc tggaaggata ggcgacaggg cgattccagc tgatgagttc   2160
gacccgacga agcaccgcta cgatgcggaa tactacatcg agaaccaggt tctcccggcg   2220
gtggagagga ttctaaaagc cttcggctat cggaaggagg atttgcgcta ccagaagacg   2280
aagcaggtcg gcttgggcgc gtggctgaag gtgaagggga agaagtga                2328
```

<210> SEQ ID NO 9  
<211> LENGTH: 28  
<212> TYPE: DNA  
<213> ORGANISM: Artificial sequence  
<220> FEATURE:  
<223> OTHER INFORMATION: Fwd primer

<400> SEQUENCE: 9
cccggcggtg gaggcgattc taaaagcc                                        28

<210> SEQ ID NO 10  
<211> LENGTH: 28  
<212> TYPE: DNA  
<213> ORGANISM: Artificial sequence  
<220> FEATURE:

-continued

<223> OTHER INFORMATION: Rev primer

<400> SEQUENCE: 10
gggccgccac ctccgctaag attttcgg                                              28

<210> SEQ ID NO 11
<211> LENGTH: 30
<212> TYPE: DNA
<213> ORGANISM: Artificial sequence
<220> FEATURE:
<223> OTHER INFORMATION: Fwd primer

<400> SEQUENCE: 11
gaaggatagg cgacgcggcg attccagctg                                            30

<210> SEQ ID NO 12
<211> LENGTH: 30
<212> TYPE: DNA
<213> ORGANISM: Artificial sequence
<220> FEATURE:
<223> OTHER INFORMATION: Rev primer

<400> SEQUENCE: 12
cttcctatcc gctgcgccgc taaggtcgac                                            30

<210> SEQ ID NO 13
<211> LENGTH: 29
<212> TYPE: DNA
<213> ORGANISM: Artificial sequence
<220> FEATURE:
<223> OTHER INFORMATION: Fwd primer

<400> SEQUENCE: 13
gctacatcgt cctagcgggc tctggaagg                                             29

<210> SEQ ID NO 14
<211> LENGTH: 29
<212> TYPE: DNA
<213> ORGANISM: Artificial sequence
<220> FEATURE:
<223> OTHER INFORMATION: Rev primer

<400> SEQUENCE: 14
cgatgtagca ggatcgcccg agaccttcc                                             29

<210> SEQ ID NO 15
<211> LENGTH: 29
<212> TYPE: DNA
<213> ORGANISM: Artificial sequence
<220> FEATURE:
<223> OTHER INFORMATION: Fwd primer

<400> SEQUENCE: 15
gctacatcgt cctatgaggc tctggaagg                                             29

<210> SEQ ID NO 16
<211> LENGTH: 29
<212> TYPE: DNA
<213> ORGANISM: Artificial sequence
<220> FEATURE:
<223> OTHER INFORMATION: Rev primer

<400> SEQUENCE: 16
cgatgtagca ggatactccg agaccttcc                                             29

<210> SEQ ID NO 17
<211> LENGTH: 84
<212> TYPE: DNA
<213> ORGANISM: Artificial sequence
<220> FEATURE:
<223> OTHER INFORMATION: Template DNA

<400> SEQUENCE: 17

```
cgatcacgat cacgatcacg atcacgatca cgatcacgct gatgtgcatg ctgttgtttt    60
tttacaacag catgcacatc agcg                                           84
```

<210> SEQ ID NO 18
<211> LENGTH: 84
<212> TYPE: DNA
<213> ORGANISM: Artificial sequence
<220> FEATURE:
<223> OTHER INFORMATION: NH2 coupled template
<220> FEATURE:
<221> NAME/KEY: misc_feature
<222> LOCATION: (1)..(1)
<223> OTHER INFORMATION: NH2 group attached to 5' end

<400> SEQUENCE: 18

```
cgatcacgat cacgatcacg atcacgatca cgatcacgct gatgtgcatg ctgttgtttt    60
tttacaacag catgcacatc agcg                                           84
```

<210> SEQ ID NO 19
<211> LENGTH: 2328
<212> TYPE: DNA
<213> ORGANISM: Artificial sequence
<220> FEATURE:
<223> OTHER INFORMATION: Codon optimised polymerase

<400> SEQUENCE: 19

```
atgatcttag ataccgacta tatcaccgag aacggtaaac cggtgataag ggtgttcaaa    60
aaggaaaatg gcgaattcaa gatcgagtat gatagaacct cgaaccgta cttctacgcc    120 tgttgaagg acgatagtgc catcgaagat gtgaaaaaag ttaccgccaa acgtcacggc    180
accgtggtaa aggttaaacg cgccgaaaag gttcagaaga gttcctagg ccgtccgatc    240 gaggtgtgga aattgtactt taaccatccg caggatgtcc cggcgattag agatcgtatt    300
cgtgcccacc cggcggtagt ggatatctat gagtacgata tcccgttcgc aaaaagatac    360
ttgattgata aggactaat cccgatggaa ggcgatgaag aattaaccat gttagcgttc    420
tccatctcca ccctgtacca cgaaggcgaa gagttcggca ccggtccgat tctgatgatc    480
tcctacgcag acggtagcga agcacgtgtg ataacctgga gaaaaataga cctaccttac    540
gtggacgtcg taagtaccga gaaggagatg atcaaaagat tcctgagggt ggtccgtgag    600
aaggatccgg acgtactgat tacctataac ggcgataact cgacttcgc ctacttgaaa    660 aagagatctg aggaattagg catcaaattc accctgggcc gtgatggcag tgagccgaaa    720
atccaacgta tgggcgaccg cttcgccgtc gaggtgaaag gccgtataca tttcgacttg    780
tatccggtga ttaggcgtac cattaatttg ccgacctaca ccttggaagc ggtgtacgag    840
gcggtcttcg gcaagccgaa ggaaaaggtg tacgccgaag atcgcgca ggcgtgggag    900 agcggtgagg gtctagaacg tgttgcaaga tatagcatgg aggacgccaa agttacctac    960
gaattgggcc gcgagtttt tccgatggag gcccagttat ctcgtttaat tggccagtcc    1020
ctgtgggatg ttagccgcag ttctactggt aatttggtag aatggttctt actgcgcaaa    1080
gcgtataaac gtaacgagtt agcgccaaat aagccggacg aacgtgaact ggcccgtcgt    1140
```

```
cgtggtggct atgccggcgg ttacgtgaag gaaccggagc gtggcctatg ggataacatt    1200
gtgtaccttg actttagaag ctatgcggtt agcatcatca tcacccataa tgttagtccg    1260
gacacattga atcgtgaagg atgcaaagaa tatgacgtcg ccccagaggt gggccacaaa    1320
ttttgtaaag atttcccagg attcatccca gtttgttgg gtgatctgct ggaagaacgc    1380
cagaaaatca acgtaagat gaaggcgacc gtcgatccac tggagaaaaa gctattggac    1440
taccgtcagc gcctgatcaa gattttggcg aattctttct atggatacta cggctacgcc    1500
aaagcccgtt ggtattgtaa agagtgcgcc gagtctgtca ctgcctgggg tcgtgaatat    1560
atcgaaatgg tgatccgcga gctggaagag aaatttggat tcaaagtctt gtacgccgat    1620
accgatggtc tgcacgcgac cattccgggt gccgatgccg agaccgtgaa gaaaaaggcg    1680
aaagagtttt tgaaatatat caatccgaag ttgccgggat tattagaatt ggaatacgaa    1740
ggtttctatg ttcgcggctt tttcgtgacc aagaaaaaat acgccgtgat cgacgaggaa    1800
ggaaaaatta ccaccgtgg tctagagatt gttcgtcgtg actggtccga aatcgccaaa    1860
gaaacccagg cccgtgtact ggaagcgatt ttgaagcatg gcgatgtgga ggaggcggtt    1920
cgtatcgtca agaagtgac cgaaaagctg agcaagtatg aagtgccgcc ggagaaattg    1980
gtcatacacg aacaaatcac acgtgacctg cgcgattata aggcgaccgg tccgcacgtt    2040
gccgtggcga agcgtttggc ggcccgtggt gttaagattc gtccaggaac cgtgattagt    2100
tacatagtgt tgaagggcag tggtcgtatt ggtgaccgtg ccatcccggc ggatgagttt    2160
gacccgacca gcatcgtta tgacgccgaa tattatatcg agaatcaggt gctaccagcg    2220
gttgaacgta ttttgaaggc attcggctat cgtaaagaag acctgcgcta ccagaaaacc    2280
aagcaggttg gtctgggtgc ctggttgaaa gtgaaaggca aaaaataa                  2328

<210> SEQ ID NO 20
<211> LENGTH: 2328
<212> TYPE: DNA
<213> ORGANISM: Artificial sequence
<220> FEATURE:
<223> OTHER INFORMATION: Codon optimised thumb mutant polymerase

<400> SEQUENCE: 20
atgatcttag ataccgacta tatcaccgag aacggtaaac cggtgataag ggtgttcaaa      60
aaggaaaatg gcgaattcaa gatcgagtat gatagaacct tcgaaccgta cttctacgcc    120 tgttgaagg acgatagtgc catcgaagat gtgaaaaaag ttaccgccaa acgtcacggc    180
accgtggtaa aggttaaacg cgccgaaaag gttcagaaga agttcctagg ccgtccgatc    240
gaggtgtgga aattgtactt taaccatccg caggatgtcc cggcgattag agatcgtatt    300
cgtgcccacc cggcggtagt ggatatctat gagtacgata tcccgttcgc aaaaagatac    360
ttgattgata aaggactaat cccgatggaa ggcgatgaag aattaaccat gttagcgttc    420
tccatctcca ccctgtacca cgaaggcgaa gagttcggca ccggtccgat tctgatgatc    480
tcctacgcag acgtagcga agcacgtgtg ataacctgga gaaaataga cctaccttac    540 gtggacgtcg taagtaccga gaaggagatg atcaaaagat tcctgagggt ggtccgtgag    600
aaggatccgg acgtactgat tacctataac ggcgataact tcgacttcgc ctacttgaaa    660
aagagatctg aggaattagg catcaaattc accctgggcc gtgatggcag tgagccgaaa    720
atccaacgta tgggcgaccg cttgccgtc gaggtgaaag gccgtataca ttcgacttg    780 tatccggtga ttaggcgtac cattaatttg ccgacctaca ccttggaagc ggtgtacgag    840
gcggtcttcg gcaagccgaa ggaaaaggtg tacgccgaag agatcgcgca ggcgtgggag    900
```

```
agcggtgagg gtctagaacg tgttgcaaga tatagcatgg aggacgccaa agttacctac    960
gaattgggcc gcgagttttt tccgatggag gcccagttat ctcgtttaat tggccagtcc   1020
ctgtgggatg ttagccgcag ttctactggt aatttggtag aatggttctt actgcgcaaa   1080
gcgtataaac gtaacgagtt agcgccaaat aagccggacg aacgtgaact ggcccgtcgt   1140
cgtggtggct atgccggcgg ttacgtgaag gaaccggagc gtggcctatg ggataacatt   1200
gtgtaccttg actttagaag ctatgcggtt agcatcatca tcacccataa tgttagtccg   1260
gacacattga atcgtgaagg atgcaaagaa tatgacgtcg ccccagaggt gggccacaaa   1320
ttttgtaaag atttcccagg attcatccca gtttgttgg gtgatctgct ggaagaacgc    1380
cagaaaatca aacgtaagat gaaggcgacc gtcgatccac tggagaaaaa gctattggac   1440
taccgtcagc gcctgatcaa gatttttggcg aattctttct atggatacta cggctacgcc   1500
aaagcccgtt ggtattgtaa agagtgcgcc gagtctgtca ctgcctgggg tcgtgaatat    1560
atcgaaatgg tgatccgcga gctggaagag aaatttggat tcaaagtctt gtacgccgat   1620
accgatggtc tgcacgcgac cattccgggt gccgatgccg agaccgtgaa gaaaaaggcg   1680
aaagagtttt tgaaatatat caatccgaag ttgccgggat tattagaatt ggaatacgaa   1740
ggtttctatg ttcgcggctt tttcgtgacc aagaaaaaat acgccgtgat cgacgaggaa   1800
ggaaaaatta ccaccgtgg tctagagatt gttcgtcgtg actggtccga atcgccaaa     1860
gaaacccagg cccgtgtact ggaagcgatt ttgaagcatg gcgatgtgga ggaggcggtt   1920
cgtatcgtca aagaagtgac cgaaaagctg agcaagtatg aagtgccgcc ggagaaattg   1980
gtcatacacg aacaaatcac acgtgacctg cgcgattata aggcgaccgg tccgcacgtt   2040
gccgtggcga agcgtttggc ggcccgtggt gttaagattc gtccaggaac cgtgattagt   2100
tacatagtgt tgaagggcag tggtcgtatt ggtgaccgtg ccatcccggc ggatgagttt   2160
gacccgacca agcatcgtta tgacgccgaa tattatatcg agaatcaggt gctaccagcg   2220
gttgaagcta ttttgaaggc attcggctat cgtaaagaag acctgcgcta ccagaaaacc   2280
aagcaggttg gtctgggtgc ctggttgaaa gtgaaaggca aaaaataa                 2328
```

<210> SEQ ID NO 21
<211> LENGTH: 775
<212> TYPE: PRT
<213> ORGANISM: Artificial sequence
<220> FEATURE:
<223> OTHER INFORMATION: Codon optimised thumb mutant polymerase

<400> SEQUENCE: 21

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

```
Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ser Ile Ser Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Val Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525
```

```
Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
            580                 585                 590

Lys Tyr Ala Val Ile Asp Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Ala Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 22
<211> LENGTH: 775
<212> TYPE: PRT
<213> ORGANISM: Artificial sequence
<220> FEATURE:
<223> OTHER INFORMATION: Mutant polymerase

<400> SEQUENCE: 22

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110
```

```
Asp Ile Pro Phe Ala Lys Arg Tyr Leu Ile Asp Lys Gly Leu Ile Pro
            115                 120                 125
Met Glu Gly Asp Glu Leu Thr Met Leu Ala Phe Ser Ile Ser Thr
    130                 135                 140
Leu Tyr His Glu Gly Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
                180                 185                 190
Arg Phe Leu Arg Val Val Arg Glu Lys Asp Pro Asp Val Leu Ile Thr
    195                 200                 205
Tyr Asn Gly Asp Asn Phe Asp Phe Ala Tyr Leu Lys Lys Arg Ser Glu
    210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
    275                 280                 285
Lys Val Tyr Ala Glu Glu Ile Ala Gln Ala Trp Glu Ser Gly Glu Gly
    290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
    355                 360                 365
Pro Asn Lys Pro Asp Glu Arg Glu Leu Ala Arg Arg Gly Gly Tyr
    370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Tyr Ala Val Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
450                 455                 460
Arg Lys Met Lys Ala Thr Val Asp Pro Leu Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Thr Ala Trp Gly Arg Glu Tyr Ile Glu Met Val Ile Arg Glu Leu
    515                 520                 525
Glu Glu Lys Phe Gly Phe Lys Val Leu Tyr Ala Asp Thr Asp Gly Leu
```

```
                530                 535                 540
His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
770                 775

<210> SEQ ID NO 23
<211> LENGTH: 2374
<212> TYPE: DNA
<213> ORGANISM: Artificial Sequence
<220> FEATURE:
<223> OTHER INFORMATION: Mutant polymerase

<400> SEQUENCE: 23
gggcgaattg ggtacccata tgatcttaga taccgactat atcaccgaga acggtaaacc      60
ggtgataagg gtgttcaaaa aggaaaatgg cgaattcaag atcgagtatg atagaacctt     120
cgaaccgtac ttctacgcct tgttgaagga cgatagtgcc atcgaagatg tgaaaaaagt     180
taccgccaaa cgtcacggca ccgtggtaaa ggttaaacgc gccgaaaagg ttcagaagaa     240
gttcctaggc cgtccgatcg aggtgtggaa attgtacttt aaccatccgc aggatgtccc     300
ggcgattaga gatcgtattc gtgcccaccc ggcggtagtg gatatctatg agtacgatat     360
cccgttcgca aaaagatact tgattgataa aggactaatc ccgatggaag gcgatgaaga     420
attaaccatg ttagcgttct ccatctccac cctgtaccac gaaggcgaag agttcggcac     480
cggtccgatt ctgatgatct cctacgcaga cggtagcgaa gcacgtgtga taacctggaa     540
gaaaatagac ctaccttacg tggacgtcgt aagtaccgag aaggagatga tcaaagattt     600
cctgagggtg gtccgtgaga aggatccgga cgtactgatt acctataacg gcgataactt     660
```

```
cgacttcgcc tacttgaaaa agagatctga ggaattaggc atcaaattca ccctgggccg    720
tgatggcagt gagccgaaaa tccaacgtat gggcgaccgc ttcgccgtcg aggtgaaagg    780
ccgtatacat ttcgacttgt atccggtgat taggcgtacc attaatttgc cgacctacac    840
cttggaagcg gtgtacgagg cggtcttcgg caagccgaag gaaaaggtgt acgccgaaga    900
gatcgcgcag gcgtgggaga gcggtgaggg tctagaacgt gttgcaagat atagcatgga    960
ggacgccaaa gttacctacg aattgggccg cgagtttttt ccgatggagg cccagttatc   1020
tcgtttaatt ggccagtccc tgtgggatgt tagccgcagt tctactggta atttggtaga   1080
atggttctta ctgcgcaaag cgtataaacg taacgagtta gcgccaaata agccggacga   1140
acgtgaactg gcccgtcgtc gtggtggcta tgccggcggt tacgtgaagg aaccggagcg   1200
tggcctatgg gataacattg tgtaccttga ctttagaagc tatgcggtta gcatcatcat   1260
cacccataat gttagtccgg acacattgaa tcgtgaagga tgcaaagaat atgacgtcgc   1320
cccagaggtg ggccacaaat tttgtaaaga tttcccagga ttcatcccaa gtttgttggg   1380
tgatctgctg gaagaacgcc agaaaatcaa acgtaagatg aaggcgaccg tcgatccact   1440
ggagaaaaag ctattggact accgtcagcg cctgatcaag attttggcga attctttcta   1500
tggatactac ggctacgcca aagcccgttg gtattgtaaa gagtgcgccg agtctgtcac   1560
tgcctggggt cgtgaatata tcgaaatggt gatccgcgag ctggaagaga aatttggatt   1620
caaagtcttg tacgccgata ccgatggtct gcacgcgacc attccgggtg ccgatgccga   1680
gaccgtgaag aaaaaggcga agagttttt gaaatatatc aatccgaagt tgccgggatt   1740
attagaattg gaatacgaag gtttctatgt tcgcggcttt ttcgtgacca agaaaaaata   1800
cgccgtgatc gacgaggaag gaaaaattac cacccgtggt ctagagattg ttcgtcgtga   1860
ctggtccgaa atcgccaaag aaacccaggc ccgtgtactg gaagcgattt tgaagcatgg   1920
cgatgtggag gaggcggttc gtatcgtcaa agaagtgacc gaaaagctga gcaagtatga   1980
agtgccgccg gagaaattgg tcatacacga acaaatcaca cgtgacctgc gcgattataa   2040
ggcgaccggt ccgcacgttg ccgtggcgaa gcgtttggcg gcccgtggtg ttaagattcg   2100
tccaggaacc gtgattagtt acatagtgtt gaagggcagt ggtcgtattg gtgaccgtgc   2160
catcccggcg gatgagtttg acccgaccaa gcatcgttat gacgccgaat attatatcga   2220
gaatcaggtg ctaccagcgg ttgaacgtat tttgaaggca ttcggctatc gtaaagaaga   2280
cctgcgctac cagaaaacca gcaggttgg tctgggtgcc tggttgaaag tgaaaggcaa   2340
aaaataagct agcggagctc cagcttttgt tccc                                2374
```

<210> SEQ ID NO 24
<211> LENGTH: 2374
<212> TYPE: DNA
<213> ORGANISM: Artificial Sequence
<220> FEATURE:
<223> OTHER INFORMATION: Mutant polymerase

<400> SEQUENCE: 24

```
gggaacaaaa gctggagctc cgctagctta ttttttgcct ttcactttca accaggcacc      60
cagaccaacc tgcttggttt tctggtagcg caggtcttct ttacgatagc cgaatgcctt     120
caaaatacgt tcaaccgctg gtagcacctg attctcgata taatattcgg cgtcataacg     180
atgcttggtc gggtcaaact catccgccgg gatggcacgg tcaccaatac gaccactgcc     240
cttcaacact atgtaactaa tcacggttcc tggacgaatc ttaacaccac gggccgccaa     300
acgcttcgcc acggcaacgt gcggaccggt cgccttataa tcgcgcaggt cacgtgtgat     360
```

-continued

```
ttgttcgtgt atgaccaatt tctccggcgg cacttcatac ttgctcagct tttcggtcac    420
ttctttgacg atacgaaccg cctcctccac atcgccatgc ttcaaaatcg cttccagtac    480
acgggcctgg gtttctttgg cgatttcgga ccagtcacga cgaacaatct ctagaccacg    540
ggtggtaatt tttccttcct cgtcgatcac ggcgtatttt ttcttggtca cgaaaaagcc    600
gcgaacatag aaaccttcgt attccaattc taataatccc ggcaacttcg gattgatata    660
tttcaaaaac tctttcgcct ttttcttcac ggtctcggca tcggcacccg gaatggtcgc    720
gtgcagacca tcggtatcgg cgtacaagac tttgaatcca aatttctctt ccagctcgcg    780
gatcaccatt tcgatatatt cacgaccccca ggcagtgaca gactcggcgc actctttaca    840
ataccaacgg gctttggcgt agccgtagta tccatagaaa gaattcgcca aaatcttgat    900
caggcgctga cggtagtcca atagcttttt ctccagtgga tcgacggtcg ccttcatctt    960
acgtttgatt ttctggcgtt cttccagcag atcacccaac aaacttggga tgaatcctgg   1020
gaaatcttta caaaatttgt ggcccacctc tggggcgacg tcatattctt tgcatccttc   1080
acgattcaat gtgtccggac taacattatg ggtgatgatg atgctaaccg catagcttct   1140
aaagtcaagg tacacaatgt tatcccatag gccacgctcc ggttccttca cgtaaccgcc   1200
ggcatagcca ccacgacgac gggccagttc acgttcgtcc ggcttatttg gcgctaactc   1260
gttacgttta tacgctttgc gcagtaagaa ccattctacc aaattaccag tagaactgcg   1320
gctaacatcc cacagggact ggccaattaa acgagataac tgggcctcca tcggaaaaaa   1380
ctcgcggccc aattcgtagg taactttggc gtcctccatg ctatatcttg caacacgttc   1440
tagaccctca ccgctctccc acgcctgcgc gatctcttcg gcgtacacct tttccttcgg   1500
cttgccgaag accgcctcgt acaccgcttc caaggtgtag gtcggcaaat taatggtacg   1560
cctaatcacc ggatacaagt cgaaatgtat acggcctttc acctcgacgg cgaagcggtc   1620
gcccatacgt tggattttcg gctcactgcc atcacggccc agggtgaatt tgatgcctaa   1680
ttcctcagat ctcttttttca agtaggcgaa gtcgaagtta tcgccgttat aggtaatcag   1740
tacgtccgga tccttctcac ggaccaccct caggaatctt ttgatcatct ccttctcggt   1800
acttacgacg tccacgtaag gtaggtctat tttcttccag gttatcacac gtgcttcgct   1860
accgtctgcg taggagatca tcagaatcgg accggtgccg aactcttcgc cttcgtggta   1920
cagggtggag atggagaacg ctaacatggt taattcttca tcgccttcca tcgggattag   1980
tcctttatca atcaagtatc ttttttgcgaa cgggatatcg tactcataga tatccactac   2040
cgccgggtgg gcacgaatac gatctctaat cgccgggaca tcctgcggat ggttaaagta   2100
caatttccac acctcgatcg gacggcctag gaacttcttc tgaaccttt cggcgcgttt    2160
aacctttacc acggtgccgt gacgtttggc ggtaactttt ttcacatctt cgatggcact   2220
atcgtccttc aacaaggcgt agaagtacgg ttcgaaggtt ctatcatact cgatcttgaa   2280
ttcgccattt tccttttttga acacccttat caccggttta ccgttctcgg tgatatagtc   2340
ggtatctaag atcatatggg tacccaattc gccc                               2374
```